(12) United States Patent
Duke et al.

(10) Patent No.: US 10,575,790 B2
(45) Date of Patent: Mar. 3, 2020

(54) PATIENT DIABETES MONITORING SYSTEM WITH CLUSTERING OF UNSUPERVISED DAILY CGM PROFILES (OR INSULIN PROFILES) AND METHOD THEREOF

(71) Applicant: Roche Diabetes Care, Inc., Indianapolis, IN (US)

(72) Inventors: David L. Duke, Fishers, IN (US); Bernd Steiger, Roemerberg (DE); Chinmay Uday Manohar, Fishers, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 988 days.

(21) Appl. No.: 15/058,271

(22) Filed: Mar. 2, 2016

(65) Prior Publication Data
US 2017/0251980 A1    Sep. 7, 2017

(51) Int. Cl.
*A61B 5/145*    (2006.01)
*A61B 5/00*    (2006.01)
(Continued)

(52) U.S. Cl.
CPC ........ *A61B 5/7271* (2013.01); *A61B 5/14503* (2013.01); *A61B 5/14532* (2013.01);
(Continued)

(58) Field of Classification Search
CPC .... A61B 5/14532; A61B 5/72; G06K 9/6218; G06K 9/00496
See application file for complete search history.

(56) References Cited

U.S. PATENT DOCUMENTS 6,572,545 B2    6/2003   Knobbe et al.
6,575,905 B2    6/2003   Knobbe et al.
(Continued)

FOREIGN PATENT DOCUMENTS

EP    2762073 A1    8/2014
WO    0224065 A1    3/2002
(Continued)

OTHER PUBLICATIONS

Kovatchev et al., "Symmetrization of the Blood Glucose Measurement Scale and its Applications,", Diabetes Care, 1997, vol. 20, No. 11, 1655-1658.
(Continued)

*Primary Examiner* — Meredith Weare
(74) *Attorney, Agent, or Firm* — Dinsmore & Shohl, LLP

(57) ABSTRACT

A patient diabetes monitoring system with an efficient unsupervised daily monitoring profile clustering algorithm, a method, and a computer product thereof are disclosed. The system may include a physiological data input device or sensor which receives a plurality of physiological measurements to generate a dataset, a memory which stores a clustering algorithm, and a processor. The clustering algorithm when executed by the processor, causes the processor to automatically pre-process the dataset to control an amount of bias/aggressiveness from the collected unsupervised daily monitoring profiles, thereby generating a pre-processed dataset, build a similarity matrix from the pre-processed dataset, and output an optimum number of similarity clusters found by the processor from the similarity matrix.

18 Claims, 19 Drawing Sheets

(51) Int. Cl.
  *G06F 19/00* (2018.01)
  *G06F 17/16* (2006.01)
  *G06K 9/62* (2006.01)
  *G06K 9/00* (2006.01)

(52) U.S. Cl.
  CPC .......... *A61B 5/4842* (2013.01); *A61B 5/7246* (2013.01); *A61B 5/742* (2013.01); *G06F 17/16* (2013.01); *G06F 19/3468* (2013.01); *G06K 9/00496* (2013.01); *G06K 9/6218* (2013.01)

(56) References Cited

U.S. PATENT DOCUMENTS

| | | |
|---|---|---|
| 7,291,107 B2 | 11/2007 | Hellwig et al. |
| 7,395,158 B2 | 7/2008 | Monfre et al. |
| 7,785,313 B2 | 8/2010 | Mastrototaro |
| 8,579,854 B2 | 11/2013 | Budiman et al. |
| 8,579,879 B2 | 11/2013 | Palerm et al. |
| 8,684,922 B2 | 4/2014 | Tran |
| 8,734,422 B2 | 5/2014 | Hayter |
| 8,843,321 B2 | 9/2014 | Duke et al. |
| 8,977,504 B2 | 3/2015 | Hovorka |
| 9,247,901 B2 | 2/2016 | Kamath et al. |
| 2002/0106709 A1 | 8/2002 | Potts et al. |
| 2003/0212317 A1* | 11/2003 | Kovatchev ............ G16H 50/50 600/365 |
| 2004/0167464 A1 | 8/2004 | Ireland et al. |
| 2005/0074806 A1* | 4/2005 | Skierczynski ......... G16B 40/00 435/6.13 |
| 2006/0047192 A1 | 3/2006 | Hellwig et al. |
| 2006/0093222 A1* | 5/2006 | Saffer ................... G06K 9/6218 382/224 |
| 2006/0094947 A1* | 5/2006 | Kovatchev ............ G16H 50/50 600/365 |
| 2009/0105572 A1 | 4/2009 | Malecha |
| 2010/0262434 A1 | 10/2010 | Shaya |
| 2011/0071464 A1 | 3/2011 | Palerm |
| 2011/0184267 A1 | 7/2011 | Duke et al. |
| 2011/0257627 A1 | 10/2011 | Hovorka |
| 2011/0313674 A1 | 12/2011 | Duke et al. |
| 2012/0004512 A1* | 1/2012 | Kovatchev ............ G16H 50/50 600/300 |
| 2012/0165638 A1 | 6/2012 | Duke et al. |
| 2012/0166126 A1 | 6/2012 | Engelhardt et al. |
| 2012/0191361 A1* | 7/2012 | Kovatchev ............ G16H 50/50 702/19 |
| 2012/0209091 A1* | 8/2012 | Riback ................ A61B 5/14532 600/309 |
| 2012/0253840 A1* | 10/2012 | Murata ................ G06F 19/3468 705/2 |
| 2014/0005505 A1 | 1/2014 | Peyser et al. |
| 2014/0066884 A1 | 3/2014 | Keenan et al. |
| 2014/0066887 A1 | 3/2014 | Mastrototaro et al. |
| 2014/0081103 A1 | 3/2014 | Schaible |
| 2014/0083867 A1 | 3/2014 | Schaible |
| 2014/0088392 A1 | 3/2014 | Bernstein et al. |
| 2014/0100435 A1* | 4/2014 | Duke ................. A61B 5/14532 600/365 |
| 2014/0118138 A1 | 5/2014 | Cobelli et al. |
| 2014/0187887 A1 | 7/2014 | Dunn et al. |
| 2014/0188400 A1 | 7/2014 | Dunn et al. |
| 2014/0221966 A1 | 8/2014 | Buckingham et al. |
| 2014/0235981 A1 | 8/2014 | Hayter |
| 2014/0278124 A1* | 9/2014 | Rees ..................... A61B 5/4833 702/19 |
| 2015/0273147 A1 | 10/2015 | Duke et al. |

FOREIGN PATENT DOCUMENTS

| | | |
|---|---|---|
| WO | 2013/032965 A1 | 3/2013 |
| WO | 2014/106263 A2 | 7/2014 |
| WO | 2015/183689 A1 | 3/2015 |
| WO | 2015073211 A1 | 5/2015 |

OTHER PUBLICATIONS

Lucero et al., "On the Registration of Time and the Patterning of Speech Movements," Journal of Speech, Language, and Hearing Research 40: 1111-1117.

Ward, "Hierarchical Grouping to Optimize an Objective Function," Journal of the American Statistical Association, 1963, vol. 58, Issue 301, 236-244.

Kaufman et al., Finding Groups in Data: An Introduction to Cluster Analysis (1 ed.), New York: John Wiley, ISBN 0-471-87876-6 (BOOK).

Sakoe et al., "Dynamic Programming Algorithm Optimization for Spoken Word Recognition," IEEE Transactions on Acoustics, Speech and Signal Processing 26 (1): 43-49.

Takita et al., "Cluster Analysis of Self-Monitoring Blood Glucose Assessments in Clinical Islet Cell Transplantation for Type 1 Diabetes," Diabetes Care, vol. 34, 2011, 1799-1803.

International Search Report pertaining to Appln. No. PCT/US2017/019025, filed Feb. 23, 2017, 5 pages.

Written Opinion pertaining to Appln. No. PCT/US2017/019025, filed Feb. 23, 2017, 8 pages.

International Search Report pertaining to Appln. No. PCT/US2017/019013, filed Feb. 23, 2017, 5 pages.

Written Opinion pertaining to Appln. No. PCT/US2017/019013, filed Feb. 23, 2017, 8 pages.

International Search Report pertaining to PCT application No. PCT/US2017/031661, filed May 9, 2017, 6 pages.

Written Opinion pertaining to PCT application No. PCT/US2017/031661, filed May 9, 2017, 11 pages.

Kovatchev, B.P., et al., Symmetrization of the Blood Glucose Measurement Scale and its Applications, Diabetes American Diabetes Association, vol. 20., No. 11, Nov. 1, 1997, pp. 1655-1658, USA.

International Search Report pertaining to PCT application No. PCT/US2017/031662, filed May 9, 2017, 6 pages.

Written Opinion pertaining to PCT application No. PCT/US2017/031662, filed May 9, 2017, 9 pages.

Hughes, et al., Hypoglycemia Prevention via Pump Attenuation and Red-Yellow-Green "Traffic" Lights Using Continuous Glucose Monitoring and Insulin Pump Data, Journal of Diabetes Science and Technology, vol. 4, No. 5, Sep. 1, 2010, pp. 1146-1155, USA.

International Search Report pertaining to Appln. No. PCT/US2017/019030, filed Feb. 23, 2017, 5 pages.

Written Opinion pertaining to Appln. No. PCT/US2017/019030, filed Feb. 23, 2017, 9 pages.

U.S. Non-Final Office Action dated Sep. 5, 2017 pertaining to U.S. Appl. No. 14/677,148, 13 Pages.

International Search Report dated Aug. 21, 2017, pertaining to PCT/US2017/029072, filed Apr. 24, 2017, 6 pages.

Written Opinion dated Aug. 21, 2017, pertaining to PCT/US2017/029072, filed Apr. 24, 2017, 14 pages.

Jaramillo et al., Prediction of Postprandial Blood Glucose Under Intra-Patient Variability and Uncertainty and its Use in the Design of Insulin Disposing Strategies for Type I Diabetic Patients, Jul. 22, 2011, pp. 1-178, URL:http://dugi-doc.udg.edu/bitstream/handle.

Pickup et al. (Continuous Subcutaneous Insulin Infusion at 25 Years, Diabetes Care 2002, 25, 593-598).

Bruno Sinopoli, et al., Kalman Filtering With Intermittent Observations, DARPA under grant F33615-01-C-1895, 28 pages.

David Di Ruscio, Closed and Open Loop Subspace System Identification of the Kalman Filter, 2009 Norwegian Society of Automatic Control, vol. 30, No. 2, 2009, pp. 71-86, ISSN 1890-1328, Norway.

J. Zico Kolter, et al., A Probabilistic Approach to Mixed Open-loop and Closed-loop Control, with Application to Extreme Autonomous Driving, Computer Science Department, Stanford University, Carolina (kolter@cs.stanford.edu), 7 pages, USA.

Chiara Toffanin, et al., Artificial Pancreas: Model Predictive Control Design from Clinical Experience, Journal of Diabetes Science and Technology, pp. 1470-1483, vol. 7, Issue 6, Nov. 2013, USA.

(56) References Cited

OTHER PUBLICATIONS

Signe Schmidt, et al., Model-Based Closed-Loop Glucose Control in Type 1 Diabetes: The DiaCon Experience, Journal of Diabetes Science and Technology, pp. 1255-1264, vol. 7, Issue 5, Sep. 2013, USA.

Schwartz et al., "Use of Automated Bolus Calculators for Diabetes Management," Diabetes Management, Touch Medical Media 2013, 92-95.

International Search Report and Written Opinion completed Jun. 10, 2016 pertaining to PCT/US2016/025502 filed Apr. 1, 2016.

U.S. Non-Final Office Action dated May 31, 2018 pertaining to U.S. Appl. No. 15/170,468, 12 pages.

Chassin et al., "Evaluation of glucose controllers in virtual environment: methodology and sample application", Artificial Intelligence in Medicine, vol. 32, 2004, pp. 171-181.

\* cited by examiner

PATIENT DIABETES MONITORING SYSTEM WITH CLUSTERING OF UNSUPERVISED DAILY CGM PROFILES (OR INSULIN PROFILES) AND METHOD THEREOF

TECHNICAL FIELD

The following disclosure is related generally to diabetes management, and in particular to a patient diabetes monitoring systems and methods that identify day(s) where a diabetes control therapy was inadequate using a clustering of similar unsupervised daily CGM profiles (or insulin profiles).

BACKGROUND

Diabetes can be characterized by hyperglycemia and relative insulin deficiency. There are two main types of diabetes, Type I diabetes (insulin-dependent diabetes mellitus) and Type II diabetes (non-insulin-dependent diabetes mellitus). In some instances, diabetes is also characterized by insulin resistance.

Insulin secretion functions to control the level of blood glucose to keep the glucose levels at an optimum level. Healthcare for a person diagnosed with diabetes may involve both establishing a therapeutic program and monitoring the progress of the afflicted person. Monitoring blood glucose levels is an important process that is used to help diabetics maintain blood glucose levels as near as normal as possible throughout the day. Monitoring can also allow successful treatment of a diabetic by altering therapy as necessary. Monitoring may allow the diabetic to monitor more closely his or her condition and, in addition, can provide information of value to the healthcare provider in determining both progress of the patient and detecting any need to change the patient's therapy program.

Advances in the field of electronics over the past several years have brought about significant changes in medical diagnostic and monitoring equipment, including self-care monitoring. In controlling and monitoring diabetes, relatively inexpensive and easy-to-use blood glucose monitoring systems have become available that provide reliable information that allows a diabetic and his or her healthcare professional ("HCP") to establish, monitor and adjust a treatment plan.

There are two main types of blood glucose monitoring systems used by patients: single point (or non-continuous) systems and continuous systems. Non-continuous systems consist of meters and tests strips and require blood samples to be drawn from fingertips or alternate sites, such as forearms and legs. An example of a non-continuous system may require a diabetic to apply a blood sample to reagent-impregnated region of a test strip, wipe the blood sample from the test strip after a predetermined period of time, and, after a second predetermined period of time, determine blood glucose level by comparing the color of the reagent-impregnated regions of the test strip with a color chart supplied by the test strip manufacturer. These systems also can rely on lancing and manipulation of the fingers or alternate blood draw sites, which can be extremely painful and inconvenient, particularly for children.

An example of a continuous system is a continuous glucose monitors ("CGM") that can be implanted subcutaneously and measure glucose levels in the interstitial fluid at various periods throughout the day, providing data that shows trends in glucose measurements over a period of time. CGMs can provide large quantities of data that need to be processed to find patterns of similar data. The data can be used to identify harmful patient behaviors or to help optimize therapy based on similar past experiences. It can also be used to monitor glucose over time to determine a blood sugar pattern. Because of the large quantities of data involved, an efficient algorithm may be needed to enable pattern analysis on devices with limited processing power. In addition, although an ambulatory glucose profile (AGP) provides both graphic and quantitative characterizations of diurnal glucose patterns, such characterizations do not provide sufficient information for HCPs to identify weak points related to therapy adherence or effectiveness.

While a variety of devices and techniques may exist for continuously monitoring a patient over time, it is believed that no one prior to the inventors has made or used the inventive embodiments as described herein.

SUMMARY

It is against the above background that according to the various embodiments disclosed herein, clustering of a dataset of unsupervised CGM data based on similar days therefore greatly enhances HCPs ability to identify problem areas (times) along the day and may help optimize therapy that focuses on these weak points. Various embodiments of the present invention disclosed herein address a way to automatically analyze unsupervised CGM profiles and cluster them based on similarity index. Various embodiments of the present invention disclosed herein also illustrate a method to determine a minimum number of similar clusters found in the dataset.

In one example, a patient diabetes monitoring system is disclosed. The system may comprise a physiological data input device which acquires a plurality of physiological measurements of the patient within a time window to generate at least one time window dataset of collected unsupervised daily monitoring profiles; a memory storing an unsupervised daily monitoring profile clustering algorithm; and a processor in communication with said input device to receive said generated at least one time window dataset, and in communication with said memory in order to execute said unsupervised daily monitoring profile clustering algorithm, wherein said unsupervised daily monitoring profile clustering algorithm when executed by said processor causes said processor automatically to: pre-process the dataset to control an amount of bias/aggressiveness from the collected unsupervised daily monitoring profiles to generate a pre-processed dataset, build a similarity matrix from the pre-processed dataset, and output an optimum number of similarity clusters found by the processor from the similarity matrix.

In another embodiment, disclosed is a non-transitory computer-readable medium that stores a program that, when executed by a processor, causes the processor to execute, via a patient diabetes monitoring system having a physiological data input device which acquires a plurality of physiological measurements of the patient within a time window to generate at least one time window dataset of collected unsupervised daily monitoring profiles and which is in communication with said processor, such that said processor receives said generated at least one time window dataset, and in communication with said memory, an unsupervised daily monitoring profile clustering algorithm that causes said processor to automatically: pre-process the dataset to control an amount of bias/aggressiveness from the collected unsupervised daily monitoring profiles to generate a pre-processed dataset, build a similarity matrix from the pre-processed dataset, and output an optimum number of similarity clusters. In another embodiment of the non-transitory computer-readable medium, CGM profile or insulin profile is the at least one time window dataset from a patient, and comprises raw data, transformed data, raw data associated with related data tags, transformed data associated with related data tags, or combinations thereof.

In yet another embodiment, disclosed is a method for identifying day(s) where a diabetes control therapy was inadequate for a patient using a monitoring system comprising a display device, a physiological data input device and a processor. The method comprises receiving automatically from physiological data input device a plurality of physiological measurements of the patient within a time window to generate at least one time window dataset of collected unsupervised daily monitoring profiles; and executing from a memory a stored an unsupervised daily monitoring profile clustering algorithm and causing the processor automatically to: pre-process the dataset to control an amount of bias/aggressiveness from the collected unsupervised daily monitoring profiles, thereby generating a pre-processed dataset, build a similarity matrix from the pre-processed dataset, and output on the display an optimum number of similarity clusters found by the processor from the similarity matrix.

While the specification concludes with claims, which particularly point out and distinctly claim the invention, it is believed the present invention will be better understood from the following description of certain examples taken in conjunction with the accompanying drawings. In the drawings, like numerals represent like elements throughout the several views.

BRIEF DESCRIPTION OF THE SEVERAL DRAWING VIEWS

Figure 16A:
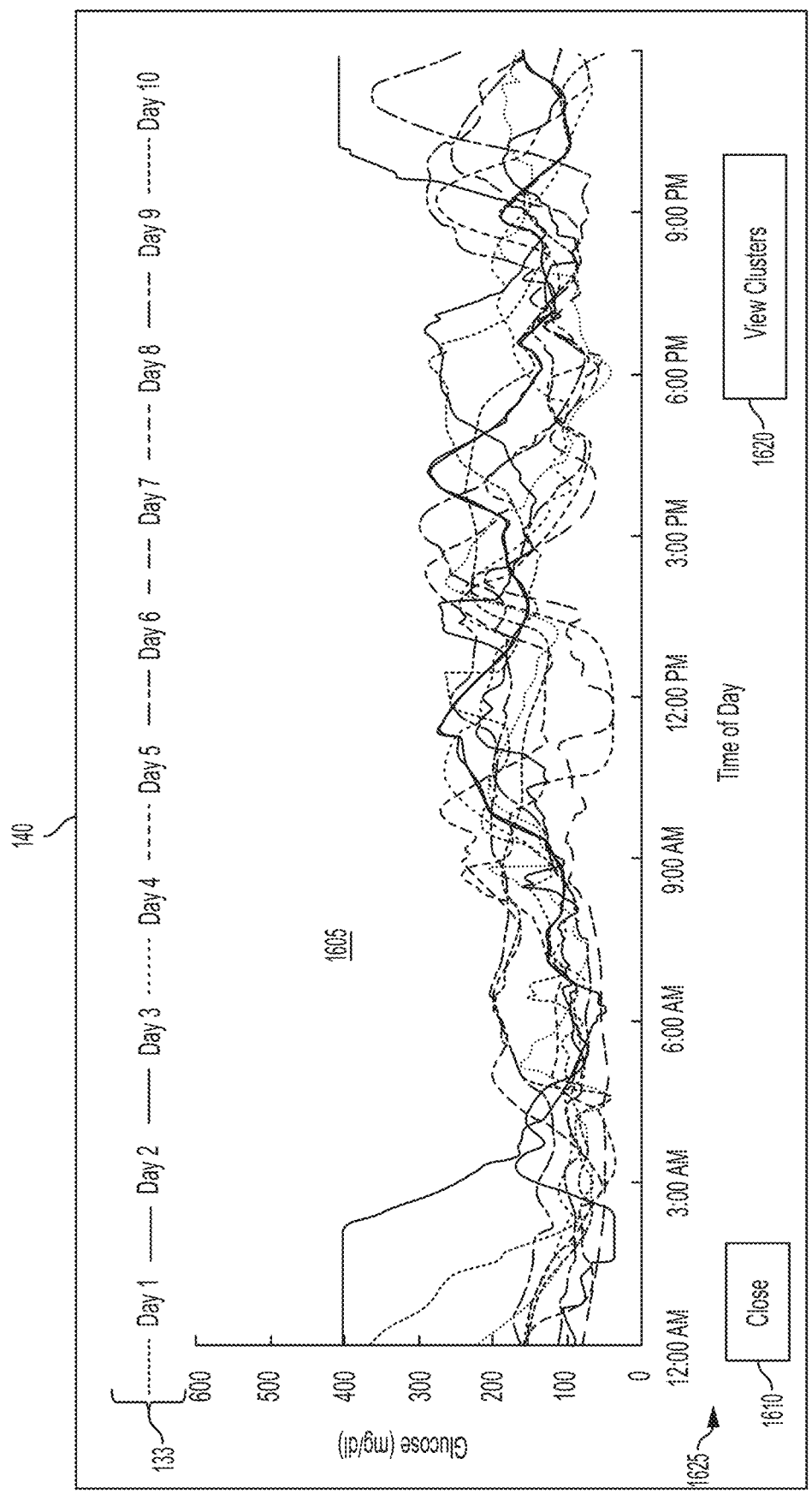
FIG. 16A depicts a displayed output of graphical plots of an original monitoring dataset.

FIGS. 16B-16F each depict a displayed output of a found minimum cluster from the original monitoring dataset depicted in FIG. 16A.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

Exemplary Devices and Methods

Figure 1:
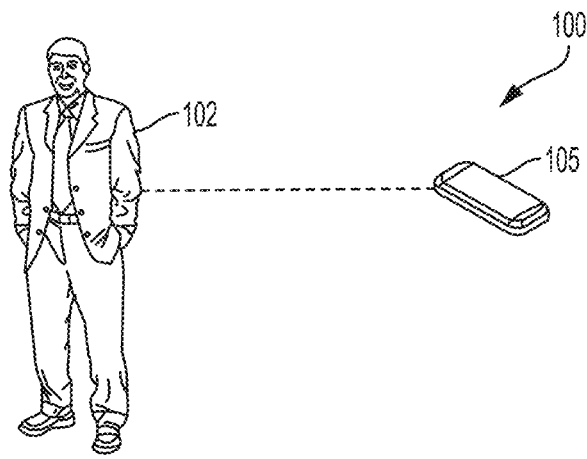
FIG. 1 depicts a diagram of an exemplary version of a patient diabetes monitoring system associated with a diabetic patient.

FIG. 1 depicts an exemplary configuration of a patient diabetes monitoring system 100 in association with a patient 102. The patient 102 may be a diabetic patient, or a patient with a physiological condition which requires routine or continuous monitoring. The monitoring system 100 comprises hardware and software components that may be utilized for implementing an unsupervised daily monitoring profile clustering feature as described further herein. As illustrated, the monitoring system 100 comprises a device 105. Device 105 may be a handheld system with limited processing power, such as a PDA, mobile phone, glucose meter, etc. Device 105 may also be a personal computer. As further shown in FIG. 2, device 105 may comprise a physiological data input device(s) 110, a data interface 115, a processor 120, a database 130, a memory 135 along with analysis logic 132, and a display 140. These components are "operably connected" to each other, which may include one or more components connected to one or more other components, either directly or through one or more intermediate components such that they may communicate and pass information as needed to perform at least the hereinafter described processes and functions. The connection may be mechanical, electrical connection, or a connection that allows transmission of signals between the components, e.g., wired or wirelessly.

The device 105 may further include an input mechanism or user interface 145 to input information and/or make data/output requests. Exemplary input mechanisms or user interfaces 145 may include a touch screen, input buttons, a keyboard, a mouse, a microphone, and combinations thereof. In one embodiment, the patient diabetes monitoring system 100 enables continuous glucose monitoring in which device 105 is operable to take multiple measurements of a concentration of glucose or a substance indicative of the concentration or presence of glucose via the physiological data input device 110, and process that dataset, e.g. a dataset 131 containing a plurality of unsupervised daily CGM glucose measurements (CGM profiles), using the processor 120 to find similar patterns represented in the dataset. As used herein, continuous (or continual) glucose monitor (or monitoring) may include the period in which monitoring of glucose concentration is continuously, continually, and/or intermittently (e.g., regularly or irregularly) performed.

Figure 2:
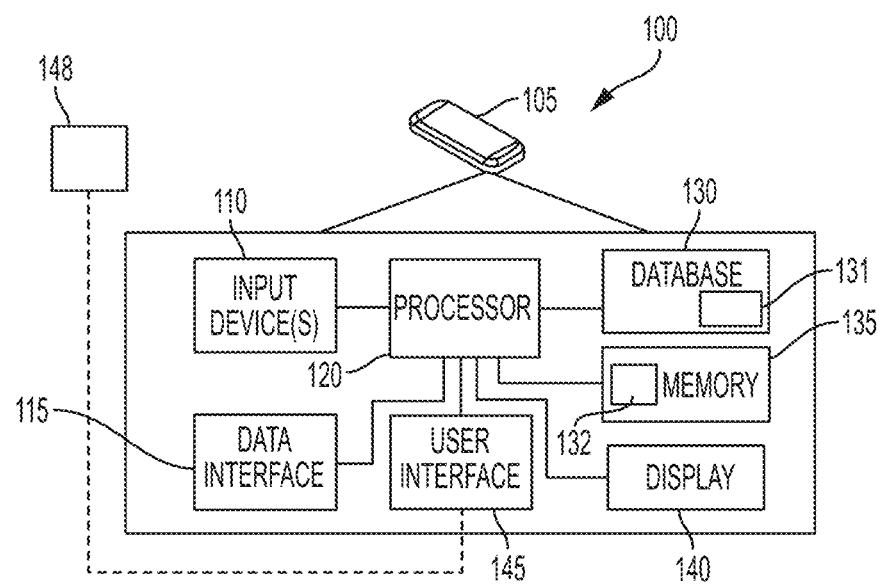
FIG. 2 depicts a block diagram of the exemplary version of the patient diabetes monitoring system of FIG. 1.

Referring to FIG. 2, the physiological data input device 110 may be, e.g., in one embodiment one or more sensors which gather automatically patient-specific physiological data such as, e.g., blood glucose, blood viscosity or other information concerning the blood chemistry of the patient 102, physical activity, temperature, heart rate, blood pressure, breathing pattern, other patient-specific physiological parameters, and combinations thereof. In one embodiment, the physiological data input device 110 can be a component or region of a patient diabetes monitoring system 100 by which glucose can be quantified and configured to produce a signal indicative of a glucose concentration of the patient 102. In operation, the physiological data input device 110 may by a glucose sensor which measures and acquires a detectable signal (e.g., a chemical signal, electrochemical signal, etc.), either directly or indirectly, from glucose or derivatives thereof that are indicative of the concentration or presence of glucose and then may transmit the signal to the processor 120 for further processing and/or storage in database 130 as a dataset 131 (illustrated only in FIG. 2 for convenience of illustration). The physiological data input device 110 may be in communication with processor 120.

As used herein, the physiological data input device 110 may be a continuous device, for example, a subcutaneous, transdermal (e.g., transcutaneous), or intravascular device. However, it should be understood that the devices and methods described herein can be applied to any device (including external devices) capable of detecting a concentration of glucose and providing an output signal that represents the concentration of glucose. The physiological data input device 110 in another embodiment can be hardware and/or software which can analyze a plurality of intermittent biological samples, for example, blood, interstitial fluid, other desired biological fluid, etc. The physiological data input device 110 can use any method of glucose-sensing, including enzymatic, chemical, physical, electrochemical, spectrophotometric, polarimetric, calorimetric, radiometric, etc. The physiological data input device 110 may use any method, including invasive, minimally invasive, and non-invasive sensing techniques, to provide an output signal indicative of, e.g., the glucose concentration or other physiological data. The output signal can be a raw data measurement that is used to provide a useful value of glucose to a user, such as a patient or physician, who may be using the device. Smoothing, evaluation methods, etc. may be applied to the raw data measurement to provide transformed data measurements to the user, such as discussed hereafter in later sections with reference made to FIG. 6.

Data measurements provided in the dataset 131 may be derived from the intermittent collection of data comprising measurements made by a device, such as e.g., the physiological data input device 110 (for example, a current measurement that ultimately corresponds to a glucose amount or concentration). The data measurements may be further associated with relevant data tags. By way of example only, a data tag may include when a meal was eaten, insulin was given, exercise took place, etc. Additionally, a data tag may include the amount of nutritional content in a meal, insulin, oral medication, exercise, etc. The data measurements may further comprise determining transformed data measurements from one or more raw data measurements and associating those transformed data measurements with relevant data tags.

The data measurements in the dataset 131 are obtained from a particular biological system (e.g., blood, interstitial fluid, etc.) using a device, such as e.g., the physiological data input device 110, maintained in operative contact with the biological system over a time window. The time window may be a defined period of time (e.g., hour(s), day(s), etc.) to obtain a series of data measurements (e.g., second(s), minute(s), hour(s), etc.) resulting in at least one time window dataset, e.g., dataset 131. The time window may be started and stopped by the diabetic patient 102 as well. By way of example only, the diabetic patient 102 may start the time window at the beginning of a meal and stop the time window at some later date after the meal. The at least one time window dataset (or data measurements) 131 may be collected from a single individual. Alternatively, the at least one time window dataset (or data measurements) 131 may be collected from multiple individuals and compiled into a database, at either the time the at least one time window dataset (or data measurements) 131 was collected or subsequently. The at least one time window dataset 131 may include raw data measurements, transformed data measurements, raw or transformed data measurements associated with data tags, or a combination thereof from the sensor.

The physiological data input device 110 may be capable of measuring only glucose in one embodiment. Alternately, in other embodiments, the physiological data input device 110 may be capable of measuring any other physiological analyte of interest that is a specific substance or component that is being detected and/or measured by chemical, physical, enzymatic, or optical analysis. The dataset 131 for each physiological analyte is collected and compiled into a multi-analyte database such as, e.g., database 130. In another example, the database 130 can also be formulated by compiling data measurements collected using multiple monitors, each of which measures a single substance, resulting in the multi-analyte database.

Examples of physiological analytes can include any specific substance, component, or combinations thereof that one is desirous of detecting and/or measuring in a chemical, physical, enzymatic, or optical analysis. Such physiological analytes include, but are not limited to, urate/uric acid, glucose, urea (blood urea nitrogen), lactate and/or lactic acid, hydroxybutyrate, cholesterol, triglycerides, creatine, creatinine, insulin, hematocrit, and hemoglobin), carbonate, calcium, potassium, sodium, chloride, bicarbonate, blood gases (e.g., carbon dioxide, oxygen, etc.), heavy metals (e.g., lead, copper, etc.), lipids, amino acids, enzyme substrates or products indicating a disease state or condition, other markers of disease states or conditions, etc. In the case of multi-analyte data databases, all of the physiological analytes may be related to a single physiologic state or condition; alternatively, in other embodiments, each physiological analyte may be relevant to a different physiological state or condition.

In still other embodiments, one or more of the above described physiological data/information may be entered manually by the patient 102 to be included in the dataset 131, as well as requested for output (e.g., displayed on display 140, sent to another external device via data interface 115, etc.), via the user interface 145. In still other embodiments, the input device 110 may also include, for example, a controller, microcontroller, processor, microprocessor, etc. that is configured to receive and/or process signals, communicate with processor 120, and generate a CGM profile (or insulin profile). The CGM profile (or insulin profile) can be the most recent dataset 131 (e.g., the most recent at least one time window dataset gathered by the input device 110, a dataset from the current day, hour(s), minute(s), etc. provided in memory 135 and/or database 130) and/or for any other dataset of interest, e.g., historical data (previous day(s), week(s), month(s), year(s), etc.) of the patient 102. The dataset 131 can be provided from the input device 110, the database 130, the memory 135, the user interface 145, and/or from any another external source of patient data that the device 105 may communicate with via the data interface 115. It is to be appreciated that as such the CGM profile (or insulin profile) can be generated from any of the data available to the device 105, and by any method performed by the processor 120, the input device 110 (if provided with processing means), or an external device(s) operating on the data (and provided to the device via the data interface 115), in which to provide on the display 140), a pattern(s) of interest such as e.g., one or more glucose curves 133 depicted by FIG. 16A.

Exemplary methods for generating a glucose curve 133 may include: having the processor 120 draw a glucose curve using glucose data measurements provided by the physiological data input device 110, having the processor 120 draw a glucose curve using glucose data measurements read from database 130 and/or memory 135 for the at least one time window or other time periods, having the processor 120 draw a glucose curve using input received via the user interface 145, having the processor 120 select a glucose curve that represents a common behavior or condition (e.g., falling blood glucose during exercise, rise of blood glucose after a meal, etc.) that may be detected in the data of the patient 102, and combinations thereof. In other embodiments, the glucose curve need not be selected from actual glucose data measurements as discussed above in regard to historical and/or external data. The CGM profile (or insulin profile) can also be generated from data resulting from a query inputted via the user interface 145 and run by the processor 120 on recent data gathered by the input device 110 or stored data provided in database 130, memory 135 and/or in other external sources that were queried by the processor 120 via data interface 115. The CGM profile (or insulin profile) may also include any relevant data tags or multi-analyte data, and the generated and/or received CGM profile (or insulin profile) may be stored in the database 130 and/or memory 135 until needed by the processor 120 for an unsupervised daily monitoring profile clustering process discussed hereafter in a later section.

The data interface 115 may be hardware and/or software which provides the device 105 with the ability to communicate wired and/or wirelessly with other devices and components as discussed hereafter in some embodiments, as well as to read from and write to non-transitory computer-readable products or storage medium, such as non-transitory computer-readable medium 148, in other embodiments. For the purposes of this description, a non-transitory computer readable product or storage medium can be any apparatus that can contain or store, programs and/or code for use by or in connection with processor, apparatus or devices. Examples of a non-transitory computer readable product or storage medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Still referring to FIG. 2, the processor 120 may include any general purpose processors or any processing component configured to provide, receive and execute a sequence of instructions (such as from the memory 135). For example, processor 120 may perform calculations using at least one time window dataset 131 (or data measurements) from the physiological data input device 110 and/or the CGM profile (or insulin profile) from input device 110 (when provided with processing means), which may also be viewed as a time window dataset 131 that is generated by the input device 110. In another example, processor 120 may also compress the at least one time window dataset 131 (or data measurements) to a reduced-rank basis as will be described further herein. In another example, processor 120 may perform unsupervised daily monitoring profile clustering with at least one time window dataset 131 (or data measurements) as will be described further herein. Processor 120 may be implemented as a single computing device or a combination of computing devices, e.g., a combination of a digital signal processor and a microprocessor, a plurality of microprocessors, one or more microcontrollers, one or more microprocessors in conjunction with a digital signal processor core, or any other such configuration.

Still referring to FIG. 2, the display 140 may comprise a liquid crystal display ("LCD"), a touch sensitive screen, a web interface, etc. A touch screen or web interface can provide a convenient way to enter various commands and/or select various programmable options. In operation, display 140 can display information, for e.g., at least one time window dataset 131 (or data measurements), unsupervised clustering results, labeled regions to identify areas of interest, data tag information, CGM profiles (or insulin profiles), etc. By way of example only, the displayed information may comprise at least one time window dataset 131 (or data measurements) that may or may not require processing by the display device prior to display. The at least one time window dataset 131 (or data measurements) displayed may be raw data, real-time data, transformed data, etc. The display 140 may comprise hardware and/or software including display instructions (e.g., software programming comprising instructions) configured to enable display of the information on display 140 and/or to obtain the information from database 130. The data in the database 130 may be queried and/or displayed by the processor 120 on the display 140.

Still referring to FIG. 2, memory 135 may be any type of memory known in the art including, but not limited to, hard disks, magnetic tape, optical disc, semi-conductor memory, a floppy diskette, a CD-ROM, a DVD-ROM, RAM memory, a remote site accessible by any known protocol, or any other memory device for storing algorithms and/or data. In operation, memory 135 may include hardware and software for clustering of unsupervised daily monitoring diabetes or insulin profiles, such as e.g., via included analysis logic 132. The analysis logic 132 may be suitably configured to store, interpret and process incoming information and/or to configure the processor 120 to perform such storing, interpreting, and processing of the incoming information, which, e.g., may be the at least one time window dataset 131, raw or transformed, etc. received from the input device 110, the user interface 145, and/or resulting from a query on available data from the input device 110, the database 130, memory 135 and/or external sources via the data interface 115. As will be discussed in greater detail below, the analysis logic 132 may include a profile-clustering algorithm for performing a clustering of unsupervised daily monitoring diabetes or insulin profiles, one or more storage algorithms, one or more data pre-processing algorithm, and/or an initialization algorithm.

Again referring to FIG. 2, database 130 may comprise memory capable of receiving and storing the measured and/or detected and/or identified characteristic information, e.g., at least one time window dataset 131, raw data measurements (e.g., numeric values which correspond to a physical measurement), compressed data measurements, transformed data measurements, and may include additional related information, e.g., data tags, pointers, etc. as described above, and/or one or more storage algorithms. When the one or more storage algorithms are executed by the processor 120, it causes the processor 120 to store at least one time window dataset 131, raw data measurements, compressed data measurements, transformed data measurements, a single numeric result calculated or derived from one or more raw data points, etc., in database 130. The processor 120 may also be caused to read at least one time window dataset 131, raw data measurements, compressed data measurements, transformed data measurements, etc. from database 130. The processor 120 may also be caused to index the at least one time window dataset 131, raw data measurements, compressed data measurements, transformed data measurements, etc. from the input device 110 as a function of the time and/or date. The database 130 may collect and receive data measurements automatically via the input device 110 over the window of time, thereby generating and storing the time window dataset 131. The data of the dataset 131 may be stored in a specialized data structure format for organizing and storing data. Exemplary data structure types may include the array, the file, the record, the table, the tree, etc. The data structure may be designed to organize data to suit a specific purpose so that it can be accessed and worked with accordingly by the functions of the system 100.

Figure 3:
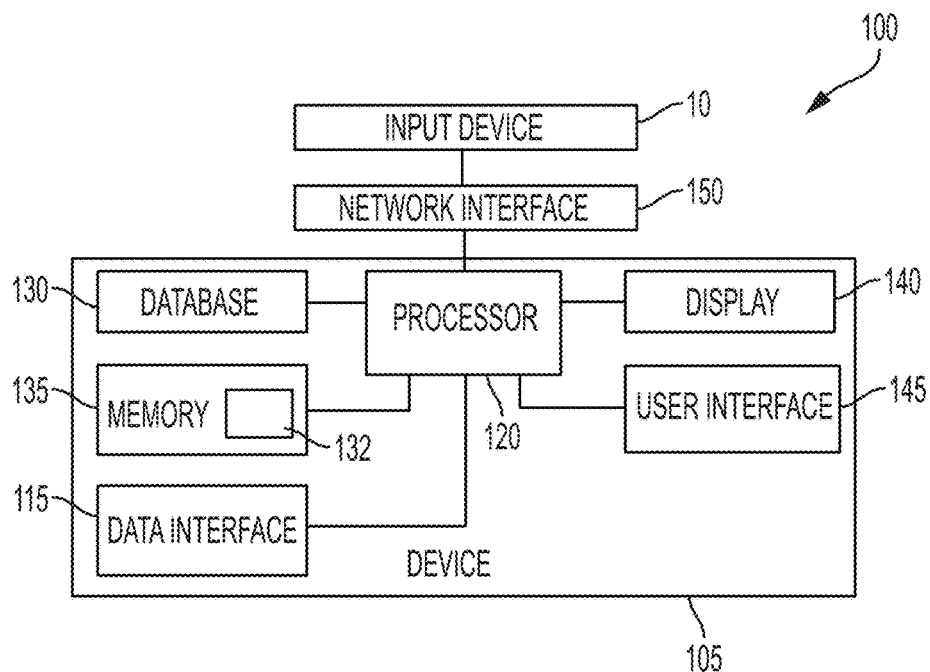
FIG. 3 depicts a block diagram of an exemplary version of a patient diabetes monitoring system.

FIG. 3 depicts another exemplary configuration of a patient diabetes monitoring system 100, and which hereafter only the difference from the configuration depicted by FIG. 2 are discussed hereafter for purposes of brevity. In this embodiment, the patient diabetes monitoring system 100 comprises device 105, input device 110 as a separate component from device 105, and a network interface 150. Device 105 comprises data interface 115, processor 120, database 130, memory 135 along with analysis logic 132, display 140, and user interface 145. The input device 110 is coupled to device 105 via the network interface 150. The network interface 150 may include a wired or wireless connection, and any wired or wireless networking hardware, such as a modem, LAN port, wireless fidelity (Wi-Fi) card, WiMax card, mobile communications hardware, and/or other hardware for communicating with other networks and/or devices. Device 105 may carry out the data storage, unsupervised daily monitoring profile clustering and display of the clustering results via use of the analysis logic 132.

Figure 4:
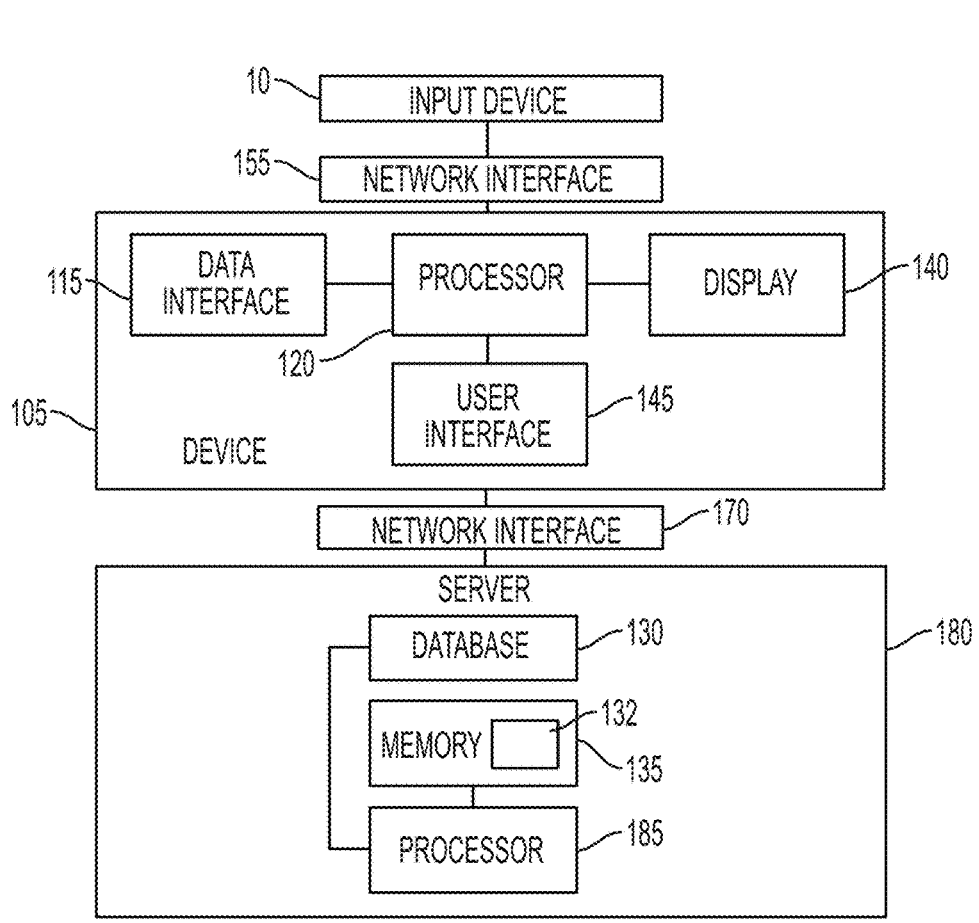
FIG. 4 depicts a block diagram of an exemplary version of a patient diabetes monitoring system.

FIG. 4 depicts another exemplary configuration of a patient diabetes monitoring system 100, and which hereafter only the difference from the configuration depicted by FIG. 3 are discussed hereafter for purposes of brevity. In this embodiment, the patient diabetes monitoring system 100 comprises device 105, the input device 110 as a separate component from device 105, a first network interface 155, a second network interface 170, and a server 180. The input device 110 may provide input to device 105 via the first network interface 155. Device 105 may be coupled to server 180 via a second network interface 170. As noted above with the network interface of FIG. 3, the first and second network interfaces may also include a wired or wireless connection, and any wired or wireless networking hardware for communicating with networks and/or devices. Device 105 comprises data interface 115, processor 120, display 140, and user interface 145. Device 105 may handle data pre-processing, inputting of data request, inputting of data queries, and display of data results. Server 180 comprises the database 130 and memory 135 along with analysis logic 132. In one example, server 180 may also comprise a processor 185 that may be configured to store data measurements into database 130 and perform unsupervised daily monitoring profile clustering via use of the analysis logic 132.

Figure 5:
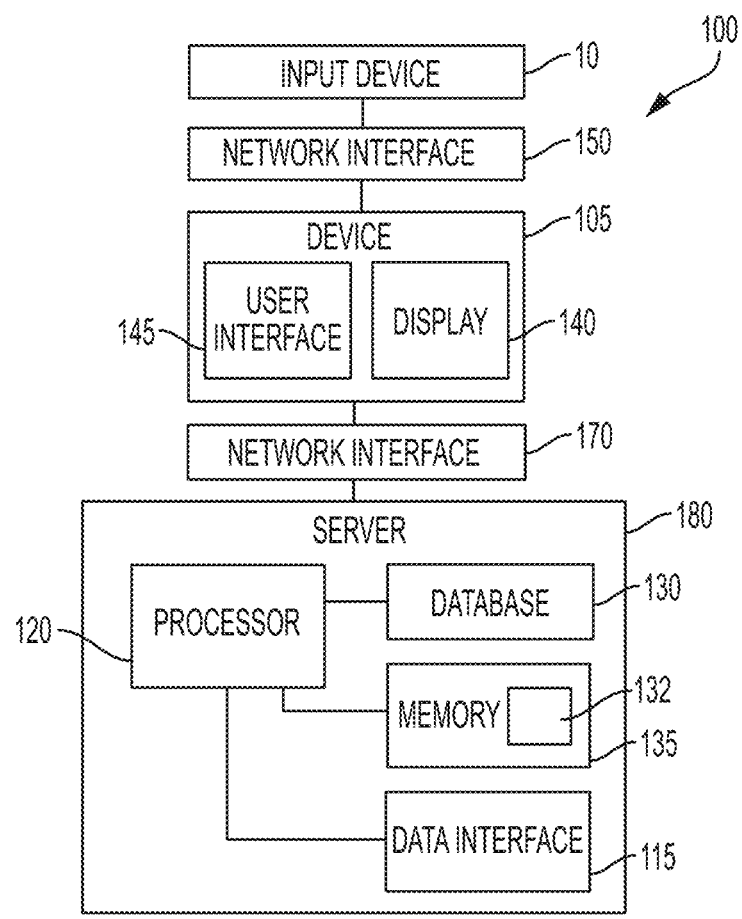
FIG. 5 depicts a block diagram of an exemplary version of a patient diabetes monitoring system.

FIG. 5 depicts another exemplary configuration of a patient diabetes monitoring system 100, and which hereafter only the difference from the configuration depicted by FIG. 5 are discussed hereafter for purposes of brevity. In this embodiment, the patient diabetes monitoring system 100 comprises device 105, input device 110 as a separate component from device 105, a first network interface 155, a second network interface 170, and a server 180. Device 105 comprises a display 140 and user interface 145, and is configured to send raw data to server 180. Server 180 comprises data interface 115, processor 120, database 130, and memory 135 along with analysis logic 132. Server 180 is configured to compress the raw data measurements, store data into database 130 and perform via use of the analysis logic 132 unsupervised daily monitoring profile clustering, which is discussed hereafter in reference to FIG. 6.

Figure 6:
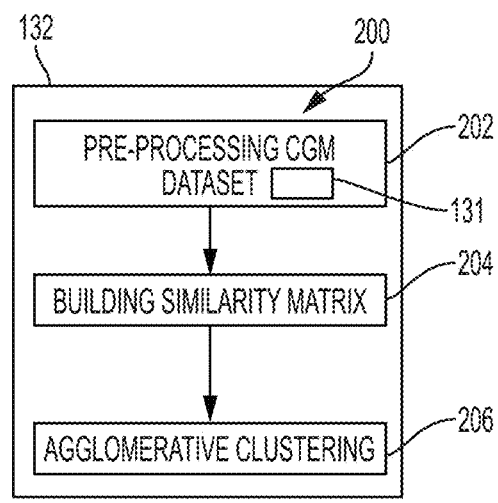
FIG. 6 depicts a flowchart of an exemplary unsupervised daily monitoring profile clustering process using a patient diabetes monitoring system.

FIG. 6 depicts a flowchart illustrating the general logic of an unsupervised daily monitoring profile clustering algorithm 200 that comprises the following processes: pre-processing 202, a building of a similarity matrix 204 and a process of agglomerative clustering 206. The clustering of similar unsupervised daily monitoring CGM profiles (or insulin profiles) by the analysis logic 132 help to identify day(s) where a diabetes control therapy was inadequate. As used herein, the term "unsupervised" means that data is collected by device 105 daily during free-living unsupervised conditions, such as collected during the course of a person's normal daily life at home, school and/or work, as opposed to data collected according to a physician guided plan/testing regiment having controlled-living, supervised conditions. The clustering algorithm 200, as discussed in greater details hereafter, is based on both the collected unsupervised glucose data as well as a rate of change of the collected unsupervised glucose data. It is to be appreciated that the high frequency and long durations at which continuous glucose monitors capture data makes analysis of such collected data tedious and time consuming. Furthermore, healthcare professionals including general practitioners, family physicians as well as endocrinologists (dialectologists) have only limited time to interact with patients with diabetes (PwD). Therefore, there is a need for an efficient and automated way of analyzing the CGM dataset for better analysis and optimizing therapy. The clustering algorithm 200 works in a hierarchical manner and helps physician identify underlying patterns in the dataset and their similarity to other members (days) in the dataset.

Pre-Processing

The purpose of the pre-processing 202 of the dataset 131 is to control the amount of bias/aggressiveness of any penalty, either on hyper side or hypo-side, that may exist in the dataset due to the unsupervised conditions of the data collection as well as to provide a data transformation that makes the transformed data symmetric for better statistical analysis. It is to be appreciated that the current consensus of accepted normal blood sugar levels for healthy people lies between 4.0 to 6.0 mmol/L during pre-prandial state and up to 7.0 mmol/L during post prandial states. For people with diabetes (T1 or T2), recommended normal glucose levels are between 4.0-9.0 mmol/L. Outside these ranges the person is at a "risk" of hyperglycemia if above 9 mmol/L or risk of hypoglycemia if below 4.0 mmol/L. It has been proposed by others to use a hazard function for SMBG measurements to evaluate a risk associated with each BG value. Specifically, others have proposed using equation (1), often called the "Kovatchev function," as such a hazard function. Equation (1) is as follows:

$$H(g) = (1.509(\log(g)^{1.0804} - 5.381))^2 \quad (1).$$

where "H(g)" is the transformed blood glucose, and "g" is the blood glucose concentration measured in millimoles per liter. See, e.g., Kovatchev et al., "Symmetrization of the blood glucose measurement scale and its applications," *Diabetes Care*, 1997, 20, 1655-1658. The hazard function described above in equation (1) has a center at 112.5 mg/dl (6.3 mmol/L), which is referred to as optimal blood glucose concentration. Furthermore, the hazard associated with hypoglycemia rises significantly faster than hyperglycemia. This hazard function, however, is not useful for retrospective analysis of CGM data since a healthcare professional would have the same concerns for a person with postprandial peak glucose level of 12 mmol/L or 15 mmol/L even though the risk calculated by equation (1) would be significantly different, for example, as shown for illustration purposes in FIGS. 7A and 7B.

Figure 7A:
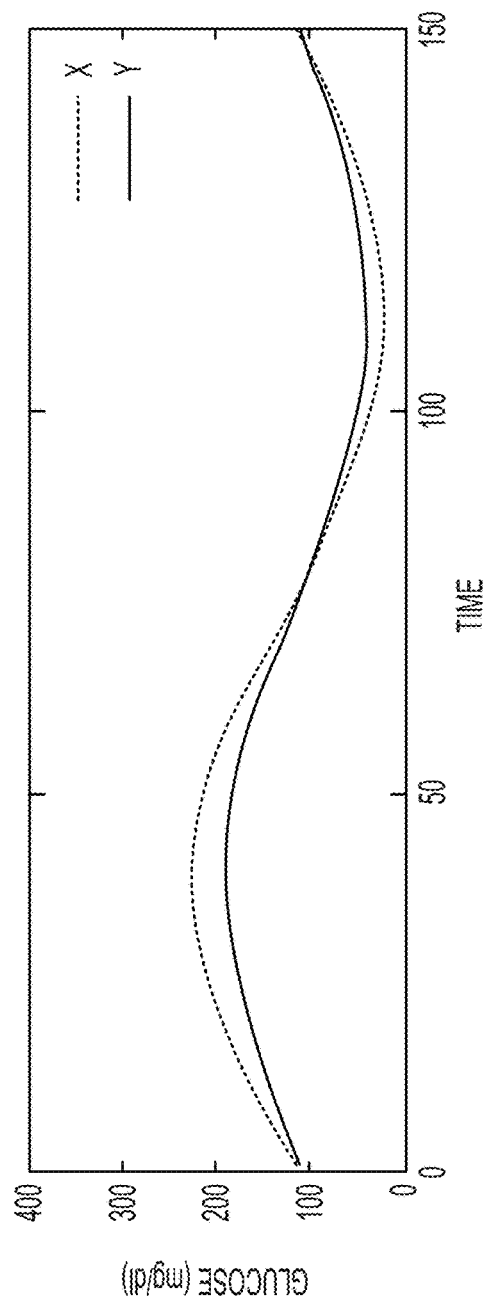
FIG. 7A depicts CGM profile traces from two days which are more or less similar but have different peak amplitudes.
Figure 7B:
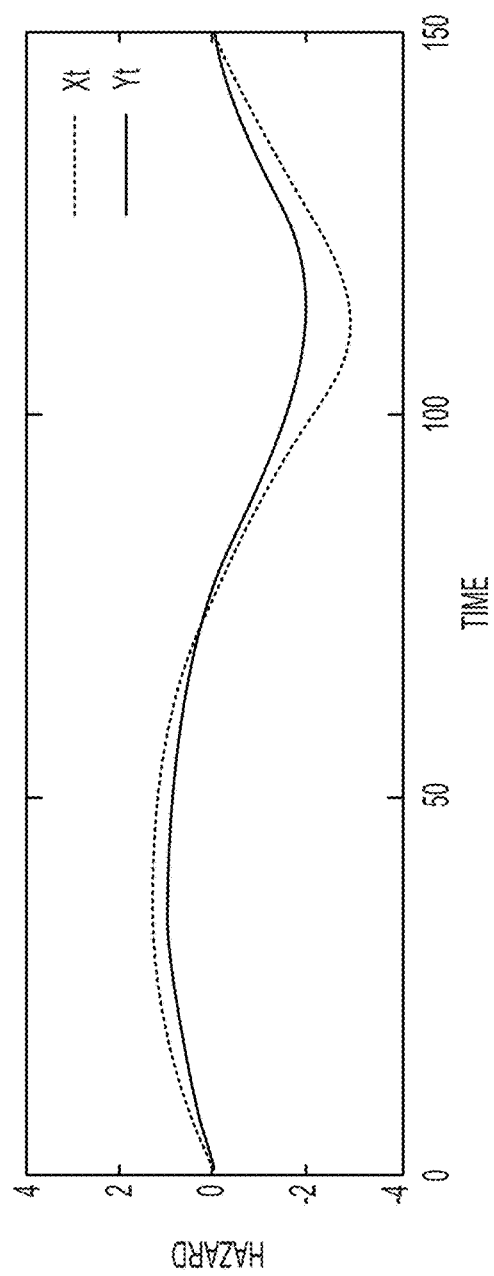
FIG. 7B depicts the CGM profile traces from FIG. 7A in a transformed space.
Figure 8:
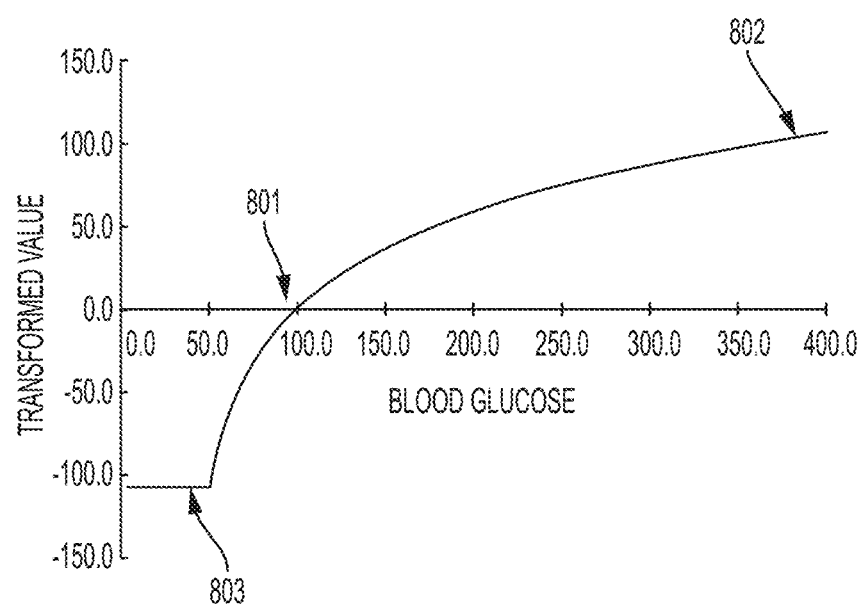
FIG. 8 depicts a proposed glucose transformation for retrospective analysis.

FIG. 7A depicts CGM profile traces for two days that are more or less similar but which have different peak amplitudes. FIG. 7B depicts the same CGM profile traces in a transformed space using equation (1). From a physician's perspective, in retrospective analysis both of the traces would be treated similarly, i.e. showing a need to 'blunt' the response on the hyper-side of the glucose response spectrum of the CGM trace. A similar need is also shown on the hypo-side of the glucose response spectrum. In view of the above, equation (2) below describes an improved transformation that is more useful for retrospective analysis than equation (1). Equation (2) is as follows:

$$G_t = \alpha * \ln(G - \beta) - \alpha * \ln(\alpha) \quad (2),$$

where parameter $\alpha = T_c - \beta$, and parameter $\beta = D_r - 1$, in which parameter $T_c$ is the center of the transformed space, parameter $D_r$ is a minimum defined glucose level, parameter $G_t$ is a transformed glucose level value, and parameter G is the original glucose level value in the dataset 131. The transformation for retrospective analysis performed on the same CGM profile traces depicted by FIG. 7A according to equation (2) is graphically depicted by FIG. 8. Compared with equation (1), equation (2) gives a better control where zero risk occurs, which is indicated by reference symbol 801 in FIG. 8. Additionally, by changing/transforming the glucose values at the upper limit, indicated by reference symbol 802, and at the lower limit indicated by reference 803, bias/aggressiveness of any penalty, either on hyper side or hypo-side, can be controlled. Furthermore, the glucose value at the lower limit 803 is chosen already in the hypo-glycemic range by parameter $D_r$, and thus from a retrospective analysis perspective, any glucose value at this level of the lower limit 803 should not have any additional risk and therefore, negative risk or the hypo-risk below the lower limit 803 is capped at the value equal to risk at the lower limit 803.

Similarity Matrix Process

When mapped with glucose along the y axis and time along the x axis, a similarity between two CGM profile traces can be computed by computing a straight line distance between data points along each of the two time series. This is known as the $L^2$ norm. For a time series vector X, with data points i=1, 2, 3 . . . n, and another time series vector $Y_i$ with members I=1, 2, 3 . . . n, the distance between the two time series vectors can be calculated according to equation (3), defined as:

$$d(X_i, Y_i) = \sqrt{\sum_{i=1}^{n} (Y_i - X_i)^2} . \quad (3)$$

Figure 9:
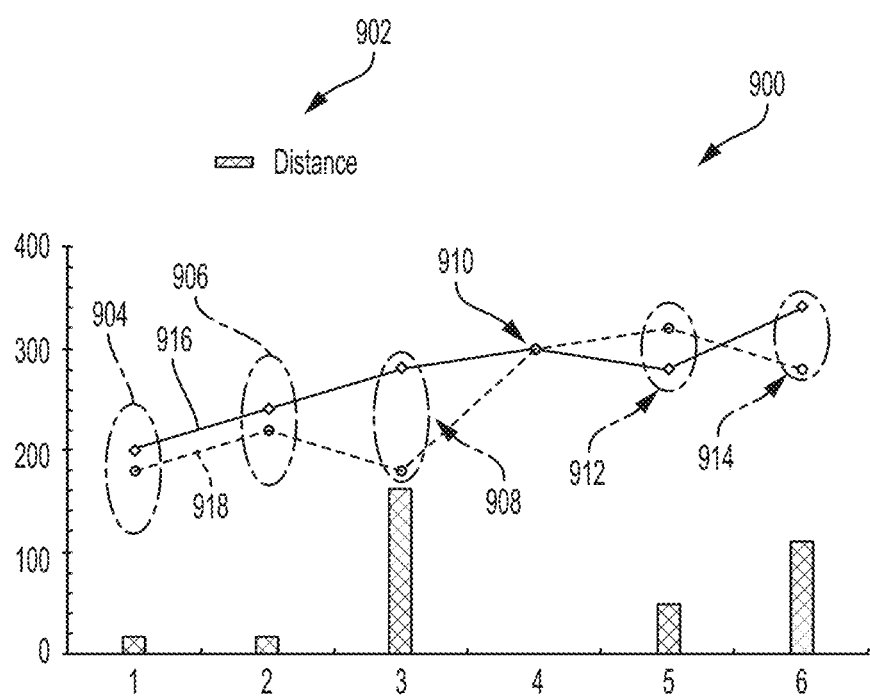
FIG. 9 depicts a distance between two points each in a respective time series.

It is to be appreciated that the Euclidean distance in equation (3) is one of the most routinely used, but such an equation fails to take into account the dynamic nature of the time series. Therefore, according to the embodiments of the present invention, a distance metric is disclosed by equation (4) which takes into account the glucose value (in actual or transformed space) and the dynamic components, i.e. slope or rate of change of glucose, to compute a distance between the two time series. Equation (4) is defined as follows:

$$d(X_i, Y_i) = k*|X_i - Y_i| + (1-k)*|(m_x - m_y)*(X_i - Y_i)| \quad (4),$$

where, parameter $X_i$—is a glucose value in a first time series X at time i; parameter $Y_i$—is a glucose value in a second time series Y at time i; parameter k—is a weighing factor; parameter $m_x$—is a slope at time i for time series Xi; and parameter $m_y$—is a slope at time i for time series Yi. The distance metric 900 of equation (4) is illustrated in the FIG. 9 depicting distance 902 between two associated points 904, 906, 908, 910, 912 and 914 each in a respective time series 916 and 918. An overall sum of each distance 902 between the two time-series 916 and 918 is computed by the algorithm 200 and then used in an elastic alignment procedure known as dynamic time warping briefly described below.

Figures 10A, 10B:
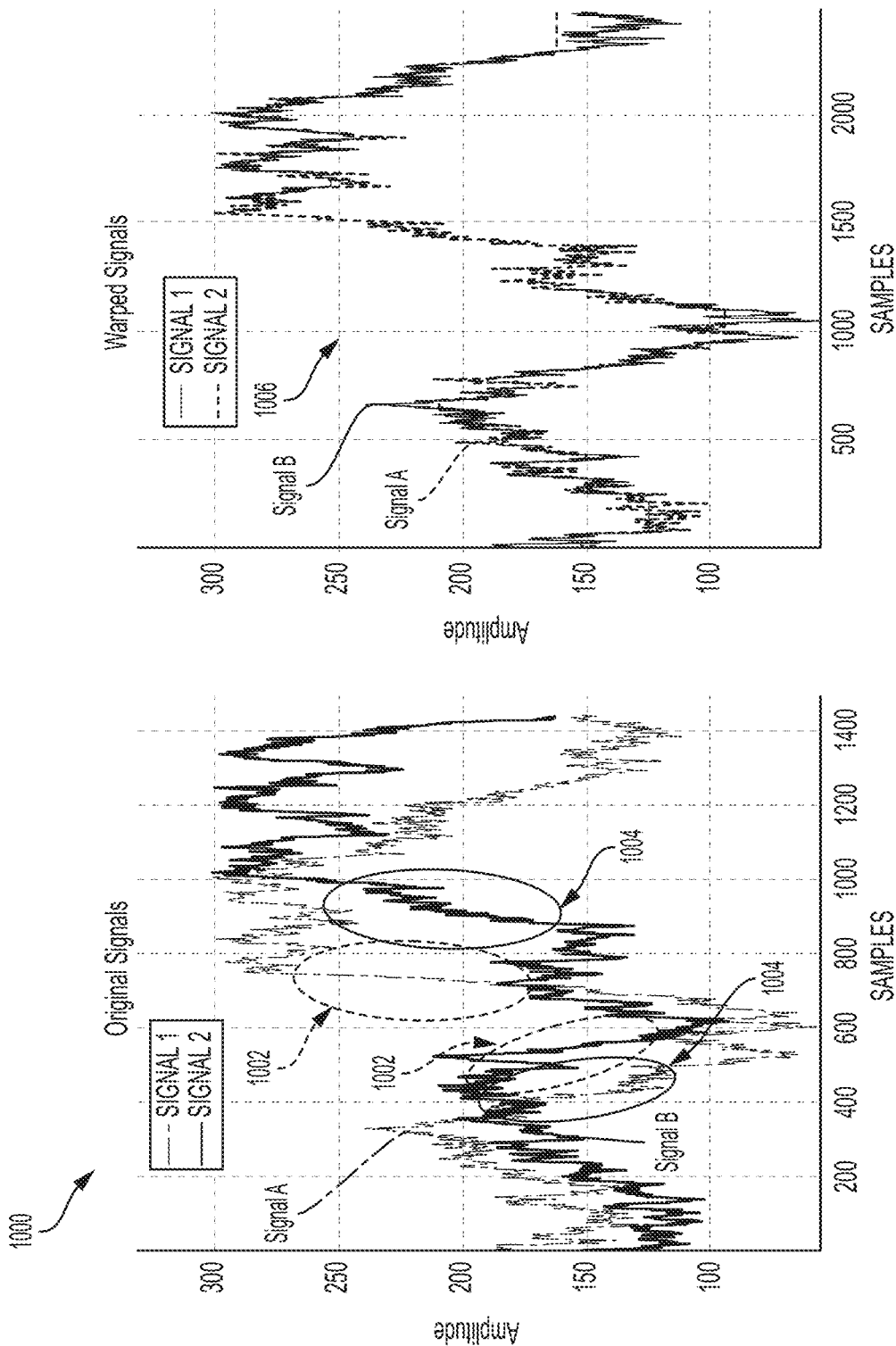
FIGS. 10A and 10B depict varying temporal responses in otherwise similar CGM profile traces.

It is to be appreciated that patient behavior may not be consistent within a day or between two days and as a result of the unsupervised CGM profile traces might show either to be out of phase, or have a delayed or compressed response to prescribed therapy such as, e.g., to a correction bolus, an insulin bolus, meals or physical activity, etc. For example, FIG. 10A shows an example of such a temporal response 1000 that may be present in the dataset 131 in otherwise similar CGM profile traces, depicted by Signals A and B. If failing to account for the varying temporal response 1000, e.g., along sections 1002 and 1004, a similar looking CGM trace would be penalized by the distance metric described above which simply uses difference in glucose values and instantaneous rate of change information, as depicted by FIG. 10B. It is therefore beneficial to further modify the above distance metric of equation (4) in the algorithm 200 during process 204 to accommodate for temporal shifts in the CGM profile traces via dynamic time warping.

Figure 11:
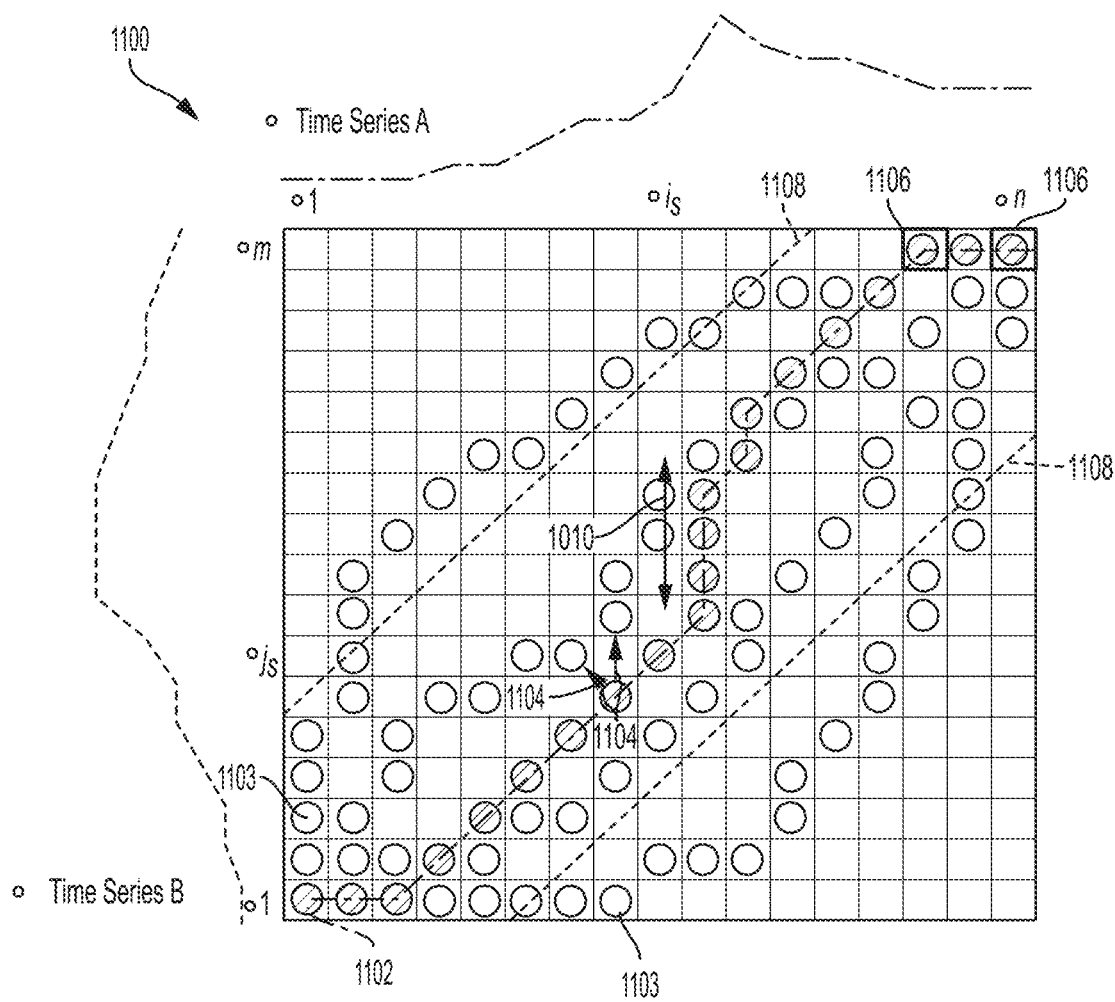
FIG. 11 depicts a general idea behind Dynamic Time Warping.

Dynamic Time warping allows for elastic matching of two time-series my local compression or elongation along time axis. See Lucero, J. C., et al.; Munhall, K. G.; Gracco, V. G.; Ramsay, J. O. (1997), "On the Registration of Time and the Patterning of Speech Movements", Journal of Speech, Language, and Hearing Research 40: 1111-1117; and see also, Sakoe, Hiroaki; Chiba, Seibi, "Dynamic programming algorithm optimization for spoken word recognition", IEEE Transactions on Acoustics, Speech and Signal Processing 26 (1): 43-49. The principal of dynamic time warping 1100 is briefly described with reference to FIG. 11. In simple terms, the goals of dynamic time warping 1100 is to find a best alignment between time-series A and time-series B shown in FIG. 11 shown by the path P (depicted by lighter dots) 1102. As depicted, the path 1102 traverses an entire length of both the time series A and B, and the function that minimizes the overall length of the path 1102 and conversely distance between curves (depicted by darker dots 1103) of the two time series A and B is called as the dynamic warping function. It is to be appreciated that the shortest alignment path 1102 thus derived in order to be considered a valid alignment path needs to meet the following conditions:

(a) Monotonicity, i.e. the path 1102 only moves forward in time;
(b) Continuity, i.e. the path 1102 cannot have breaks i.e. cannot skip data while moving forward as depicted by arrows 1104;
(c) Boundary conditions satisfied, i.e. the path 1102 has to travel entire length and does not allow some sample matching (e.g., boxes 1106);
(d) Search window satisfied, i.e., local temporal shifts of the alignment path 1102 have to be within pre-determined search width (e.g., lines 1108); and
(e) Slope satisfied, i.e. temporal compressions or elongation should not exceed a pre-determined width (e.g., line 1110).

It is to be appreciated that during the aligning process the dynamic warping function temporally compresses or elongates curves locally, which for better result, the inventors have the algorithm 200 add a penalty to the total distance between the two curves of the time series. To illustrate, first and second time series X, Y of the transformed dataset is processed with the penalty as follows:
(a) Start at origin, distance between curves of the first time series X and the second time series Y is: $X(1,1)=Y(1,1)$;
(b) Keep first row a constant distance by: $X(i,1)=X(i-1,1)+Y(i,1)$;
(c) Keep first column constant by: $X(1,j)=X(1,j-1)+Y(1,j)$; and
(d) Carry on for next row and next column to end of search space of the transformed dataset as defined by:

$$X(i,j)=\min(X(i,j-1),X(i-1,j-1),X(i-1,j))+Y(i,j) \quad (5).$$

Figure 12:
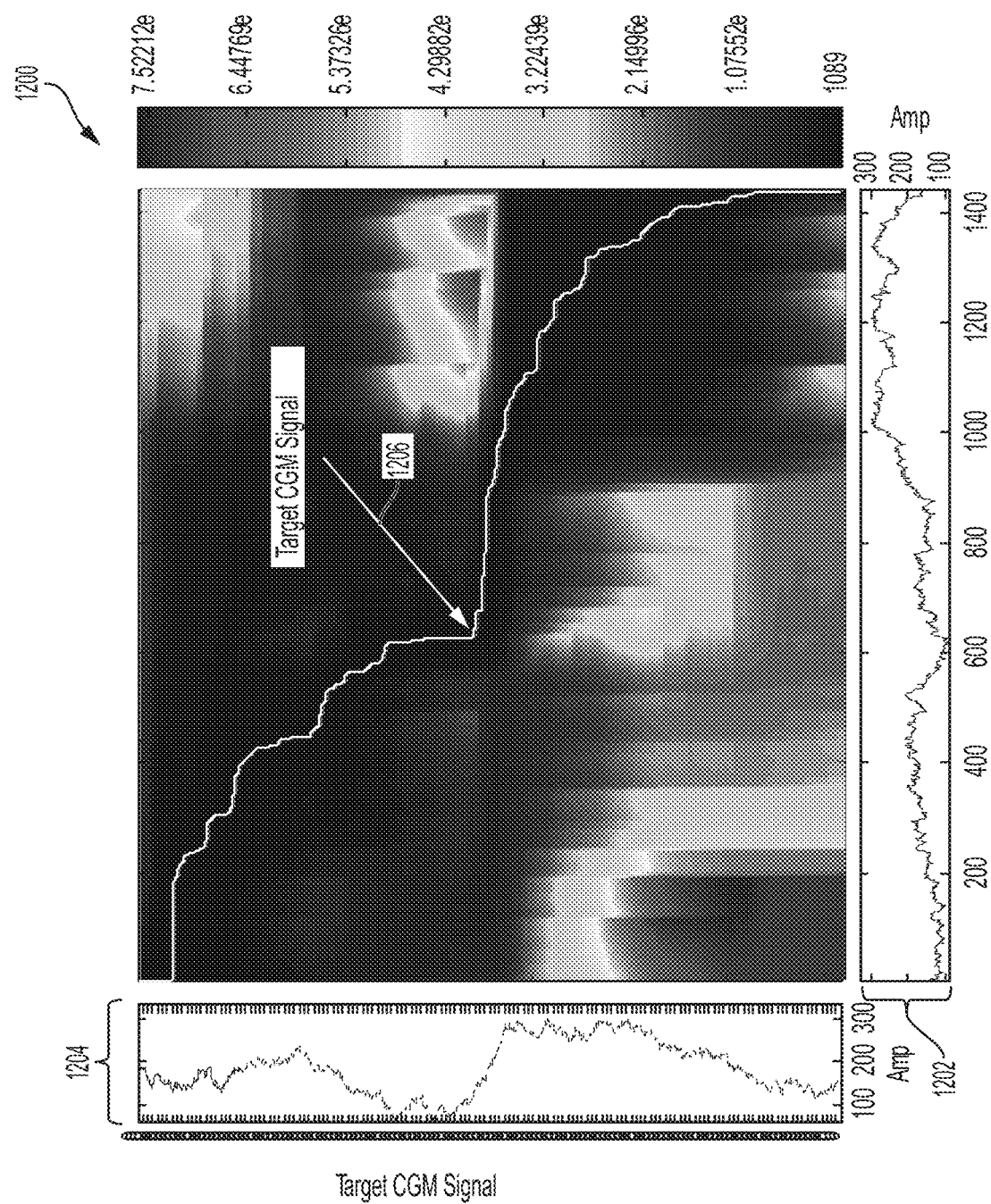
FIG. 12 depicts first and second time series of Test & Target CGM profile traces, respectively, along with a shortest alignment path taken therebetween.
Figures 13A, 13B:
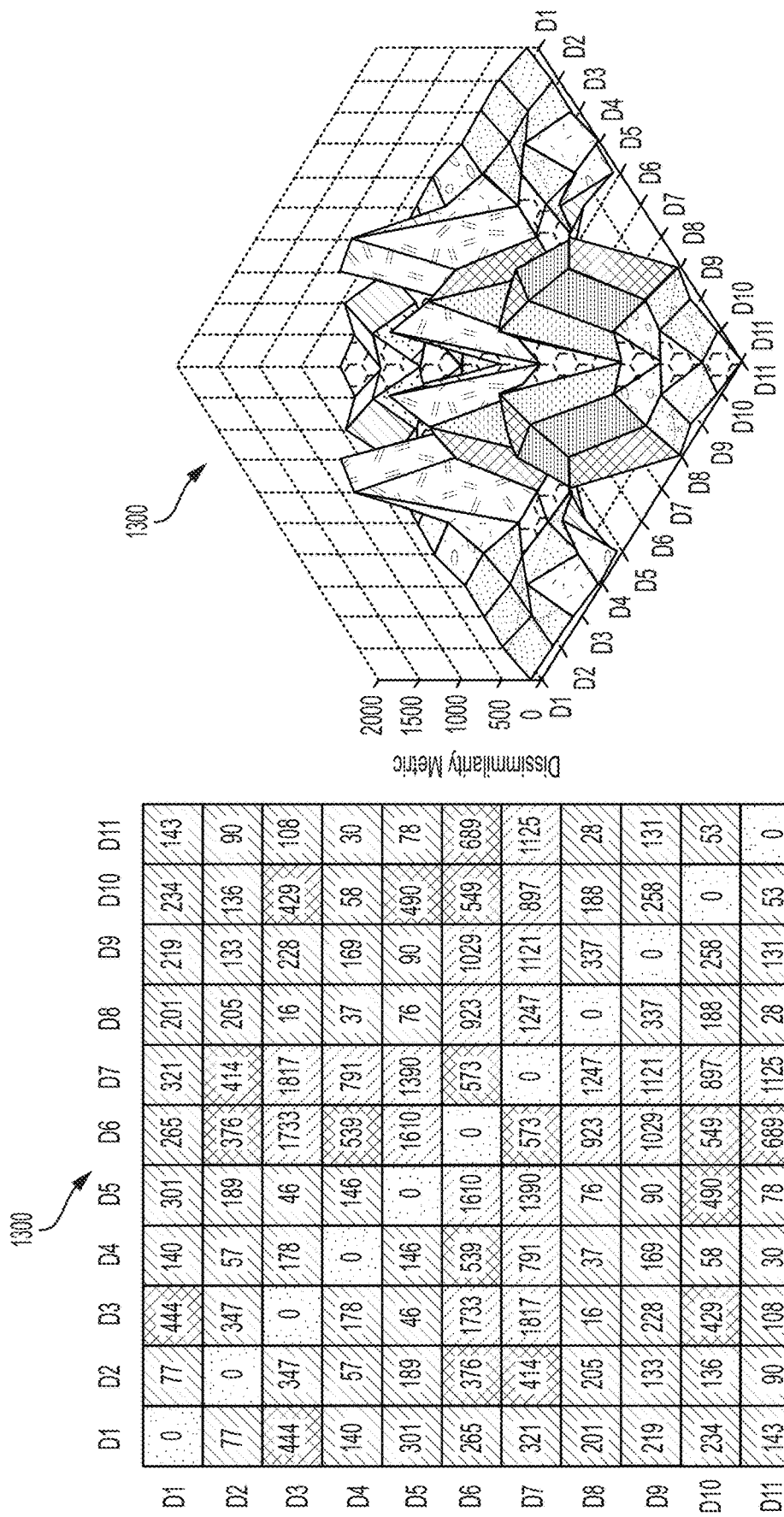
FIGS. 13A and 13B depict glucose measurement data shown arranged in a Distance Matrix and the corresponding graphical representation of the Distance Matrix, respectively.

In the equation (5) above, instead of using a simple L2 norm (Euclidean distance), the distance metric described earlier is used in equation (4). As a result when the two curves X and Y are aligned the dynamic warping function returns a total distance between the two curves accounting for differences along time axis as well as glucose values. FIG. 12 depicts such a result 1200 of the above processing in which original (Test) and warped (Target) CGM profile traces 1202 and 1204, respectively, are shown along with a shortest alignment path 1206 taken. In view of the above, the output of the similarity matrix process 204 can be summarized as follows. For a given dataset 131 with days 1 . . . n, a distance matrix according to equation (4) and modified with equation (5) is computed by measuring similarity between each day pair in the CGM profiles. Thus a dataset 131 of N days can be described using a N*N matrix as shown in FIGS. 13A and 13B. FIGS. 13A and 13B depict such output glucose measurement data from the similarity matrix process 204 in which distances are shown in a Distance Matrix of FIG. 13A and the corresponding graphical representation of the Distance Matrix is shown by FIG. 13B. The agglomeration process 206 is now discussed hereafter.

Agglomeration Process

Due to its deterministic nature hierarchical clustering yields consistent labeling, i.e. cluster members do not migrate from one cluster to another on repeated runs. See, e.g., Kaufman, L.; Rousseeuw, P. J. (1990). Finding Groups in Data: An Introduction to Cluster Analysis (1 ed.). New York: John Wiley. ISBN 0-471-87876-6. This is particularly important for example in the case of electronic consultations where the health care provider and the patient may be looking at the same dataset remotely on their respective computers, smartphones, etc. If the clustering algorithm 200 was not deterministic in nature, the HCP and the patient could potentially end up looking at different cluster members within the same labeled cluster which would result in confusion and potentially induce medical error (in correct therapy).

Using the output of the similarity matrix process 204, e.g., the distance matrix shown in FIG. 13A, the agglomerative clustering process 206 follows the following pseudo code routine: (a) Compute a distance matrix between data points of the output;
(b) Let each of the data points be a cluster;
(c) Repeat following:
   i. Merge two closest clusters, and
   ii. Update the distance matrix; and
(d) Do Repeat until only a single cluster remains.

Without pre-defined stopping condition, the above process 206 starts with each data point in the distance matrix being treated as its own cluster, in which the process automatically keeps moving forward until only one 'super' cluster remains.

Figures 14A, 14B:
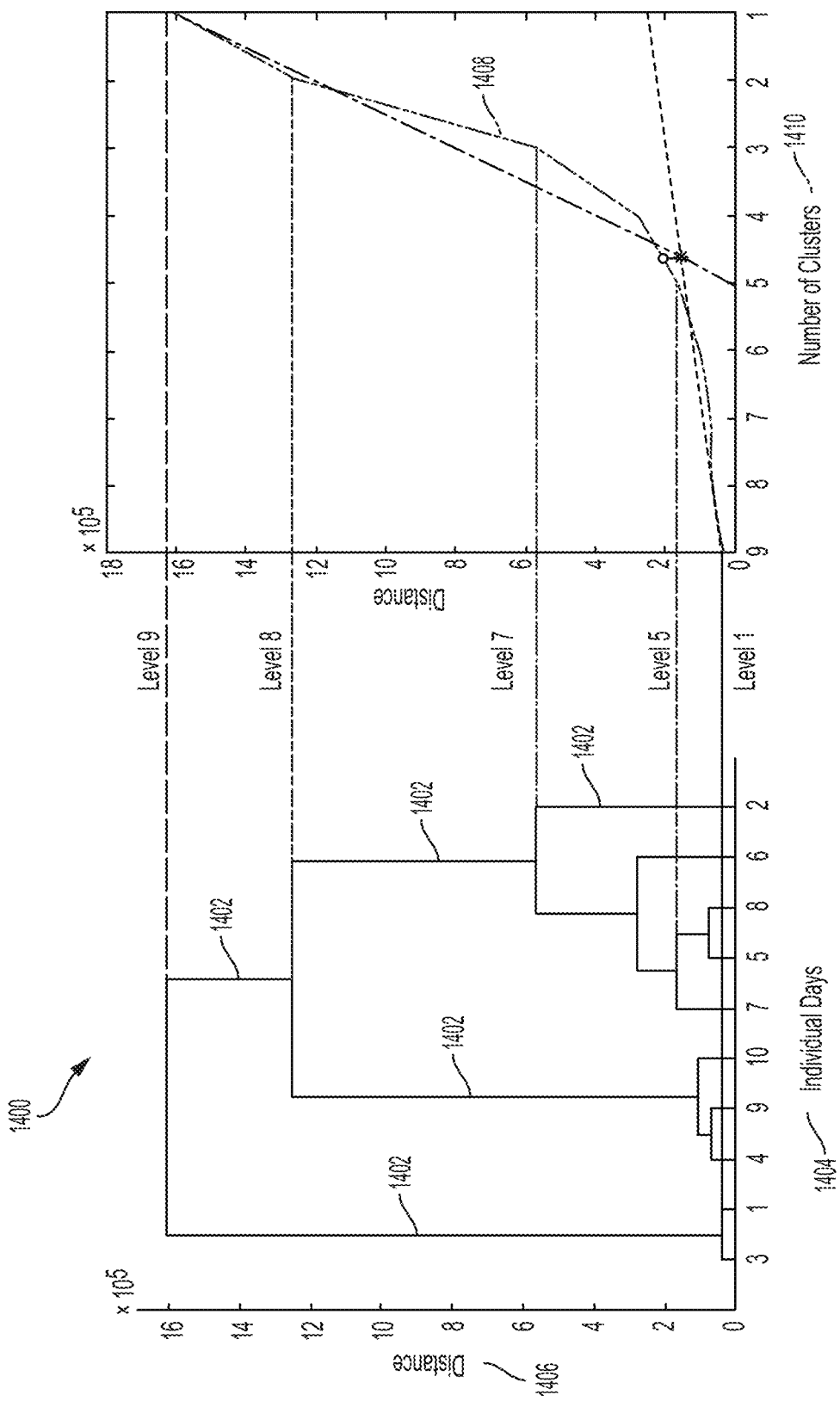
FIGS. 14A and 14B depict a dendrogram showing the 'relationship' between members of dataset, and a 'Distance' between the clusters and remaining data as merging begins, respectively.

It is to be appreciated that there are several ways to merge data points into clusters or merge two-clusters into one cluster. Perhaps the most robust method uses Ward's linkage, which minimizes the overall increase in within cluster variance. See Ward, J. H., Jr. (1963), "Hierarchical Grouping to Optimize an Objective Function", Journal of the American Statistical Association, 58, 236-244. The hierarchical clustering as the name suggests yields a relationship between the data points as the clustering progresses from one stage to another. This relationship can be represented using a tree-structure also known as dendrogram 1400 as shown in FIGS. 14A and 14B. FIG. 14A depicts how members of the dataset 131 are related to each other. Vertical lines 1402 show where two data points (Individual Days) 1404 merge via the dissimilarity or the distance 1406 between them. Although Ward's linkage ensure minimum within cluster variance, as the algorithm proceeds from Level 1 to Level 9, the dissimilarity (Distance) 1406 within the dataset 131 greatly increases as shown by the curve 1408 in FIG. 14B. At each level the number of clusters 1410 reduces by 1. For example, in case of the FIG. 14A at Level 1, data point 1 and 3 are merged and hence the number of possible clusters are 9, in which the clustering during process 206 continues all the data in the dataset 131 were grouped together to form 1 cluster at Level 9.

Finding a "right" number of clusters is perhaps one of the most challenging problems in data mining. This problem is somewhat solved by analyzing the 'relationship' as depicted in the dendrogram 1400. Each stage where the data is merged gives an indication of the similarity of the members within the dataset, which is shown FIG. 14B. Intuitively, the "right" number of clusters can be defined as a level where any addition to a cluster results in sudden increase/rise in the dissimilarity or distance curves 1408. Mathematically, this can be calculated using a second derivative test to find the inflection point or the point of concavity of the curve 1408, which discussed hereafter in reference to FIG. 15.

Figure 15:
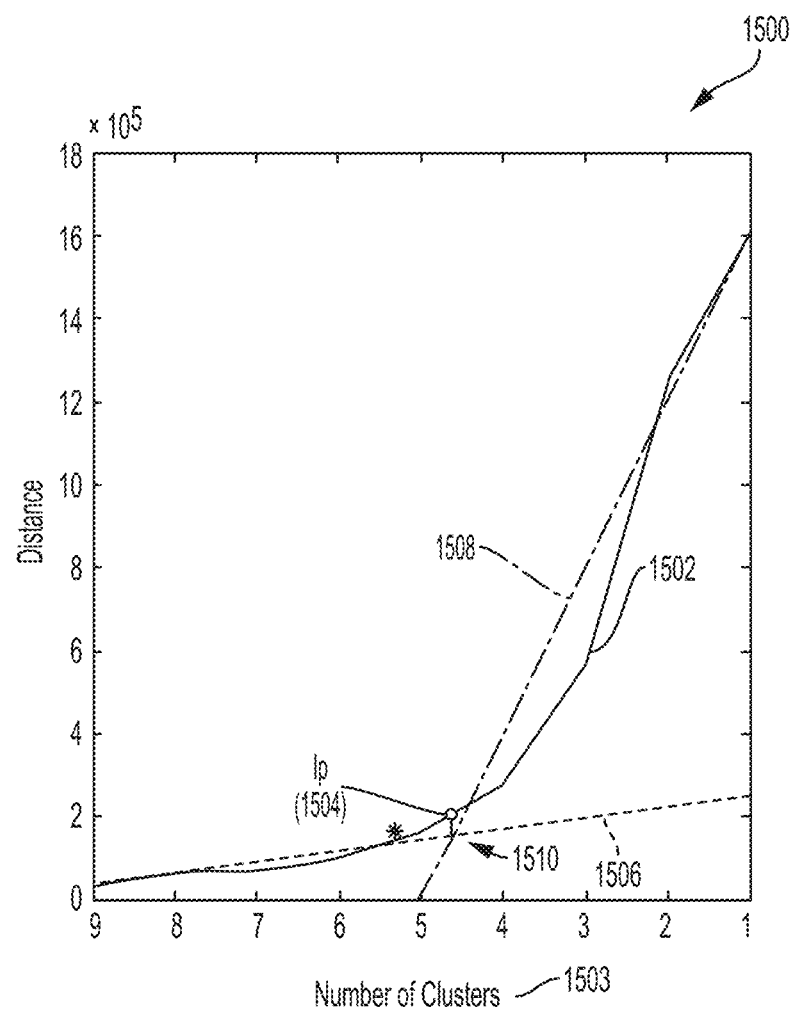
FIG. 15 depicts a graphical representation of finding minimum clusters.

A plot to find an optimum (minimum) number of clusters 1500 is graphically depicted by FIG. 15. To find the optimum number of clusters, we let d(l) be a distance curve 1502, d'(l) be a first derivative of the distance curve 1502, and d"(l) be a second derivative of the distance curve 1502. If d'(l) exists, then the optimum number of clusters along the curve d(l) may be considered point l where d"(l)=0. However, the above method works only when the distance monotonously increases as number of clusters 1503 reduce to one. A better approximation is calculating for the inflection point 1504, which is marked as a black dot on the distance curve 1502 in FIG. 15. The method to calculate the inflection point 1504 is described as follows:

(a) Let first k points on the distance curve d(l) with p points be 1, 2, . . . k, and find slopes:
$m_1 = d(2) - d(1)/(2-1)$,
$m_2 = d(3) - d(1)/(3-1)$, . . . ,
$m_k = d(n) - d(1)/(n-1)$;

(b) Calculate median of slopes from step (a): $m_a$=median $(m_1, m_2 \ldots m_k)$;

(c) Let last n points on the distance curve d(l) with p points be p-n, . . . , p-1, p, and find slopes:
$m_p = d(p) - d(p-1)/(p-(P-1))$,
$m_2 = d(P) - d(p-2)/(p-(p-2))$, . . . ,
$m_n = d(p) - d(p-n)/(p-(p-n))$; and (d) Calculate median of slopes from step (c): $m_b$=median $(m_1, m_2 \ldots m_n)$, where a first line 1506 is defined by the median slope $m_a$ with a starting point as the first point along the distance curve d(l) 1502, and a second line 1508 is defined by the median slope $m_b$ with a starting point as the end point along the distance curve d(l), such that the inflection point 1504 is a projection of an intersection point 1510 between the first and second lines 1506 and 1508 on the distance curve d(l) and denoted by $l_p$. Next in the process 206, if inflection point $l_p$ is not an integer, then the optimal minimum number of clusters $L_{min}$ is determined by the algorithm 200 in process 206 by the following:

$$L_{min} = \begin{cases} \text{floor}(lp) & \text{if } \text{abs}(l_p - \text{floor}(l_p)) < \text{abs}(l_p - \text{ceil}(l_p)) \\ \text{ceil}(lp) & \text{if } \text{abs}(l_p - \text{floor}(l_p)) > \text{abs}(l_p - \text{ceil}(l_p)) \end{cases}.$$

For example, in starting with a dataset 131 of unsupervised CGM profile traces 133 from 10 days worth of data from a diabetic user wearing a CGM, which is graphically depicted by FIG. 16A plotted all together on display 140 of device 105, and processing the dataset 131 via the analysis logic 132 with the clustering algorithm 200, five distinct clusters 1600A, 1600B, 1600C, 1600D and 1600E, each with minimum within-cluster variance were automatically determined by the processor 120. Such found minimum clusters were then provided/outputted by the processor 120 visibly distinct/discernible on the display 140 such as, for example, as each of the distinct clusters 1600A, 1600B, 1600C, 1600D and 1600E are shown by FIGS. 16B-16F, respectively. Although in FIGS. 16B-16F each glucose trace 133 determined by the processor 120 to be in a respective found cluster is shown bolded (darker) with thicker solid or dashed/dotted lines and the unrelated (non-clustered) glucose traces via respectively fainter (lighter) and thinner solid lines, the associated glucose trace(s) of each distinct minimum cluster may be made discernible from the non-associated glucose trace(s) in a number of other manners, such as by different colors and/or different line representations (dash, dot-dash, solid, darker, fainter, thinner, thicker, etc.) as well as by not displaying/hiding the non-associated glucose traces. It is to be appreciated that one of the advantages of determining, presenting and displaying the glucose traces 133 via their associated found cluster (instead of via a typical data dump display that shows all traces in the dataset, e.g., ten days worth of data with an average of 288 sampling records per day as depicted by FIG. 16A), is that rich information content provided in the dataset 131 is made discernible far easier and more effectively to a user even on a mobile device, such as a cellphone, bG meter, PDA, tablet, or similar devices, with a space-constrained display (i.e., a diagonal screen size of less than 10 inches). In other words, a device 105 provided with the above disclosed clustering functionality is more efficiently used by a user to discern days where a diabetes control therapy was inadequate than similar prior art devices without such clustering functionality and which just provide a data dump and cluttered display with numerous sampling records, such as depicted by FIG. 16A.

Figure 16B:
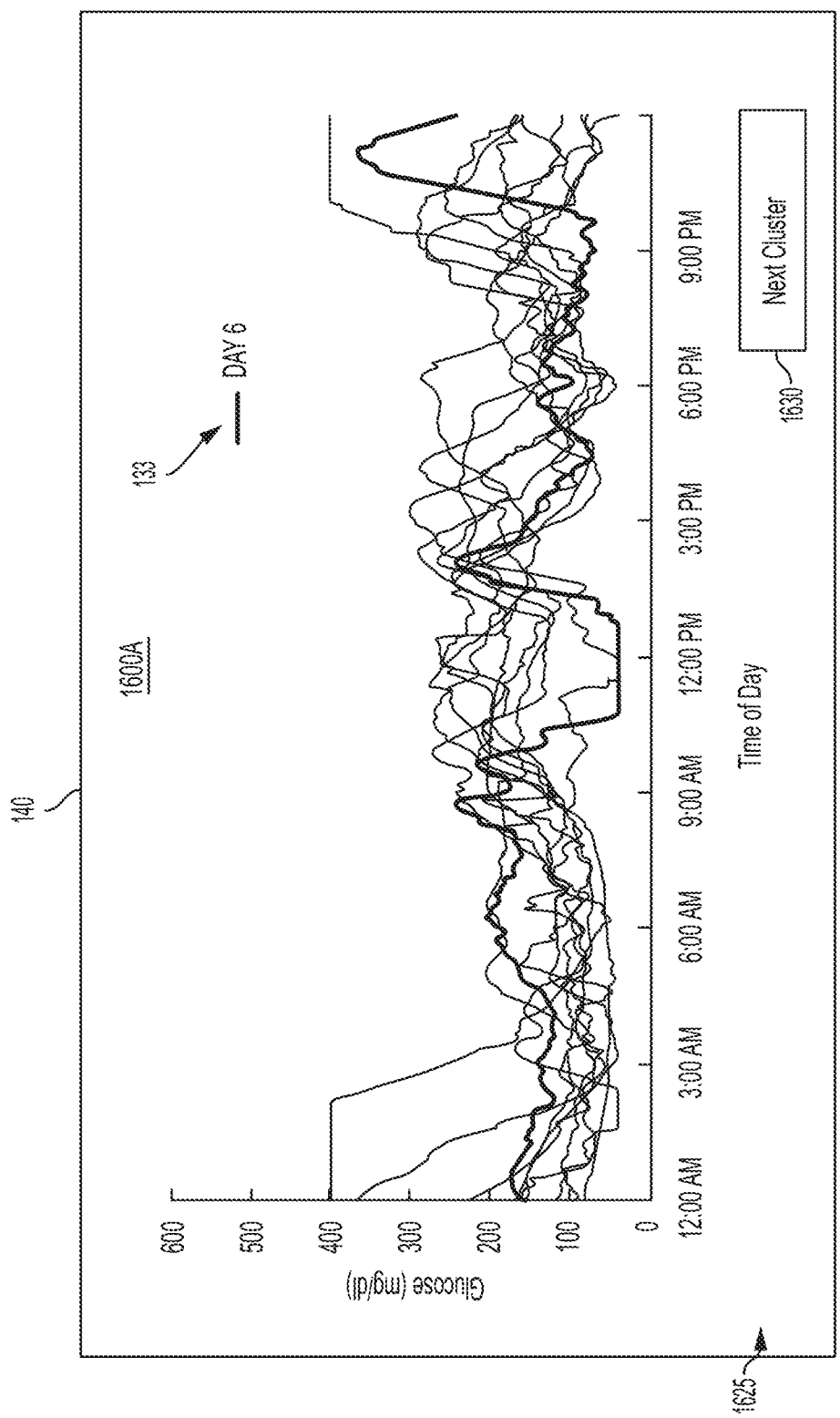

In addition, it is to be appreciated that the processor 120 in determining and producing clusters, such as the displayed clusters 1600A, 1600B, 1600C, 1600D and 1600E, based on the dataset 131 as disclosed herein, creates symbolic groupings/representations of unambiguous qualitative data regarding the sufficiency of the diabetes control therapy of the user, thereby providing a more specific and concrete way of processing and representing information (transformed via the clustering) than previously found in the prior art. For example, as depicted by FIG. 16B, the first distinct cluster 1600A determined by the processor 120 based on the dataset 131, comprises the Day 6 trace, which has been identified and highlighted as a distinct cluster due to having a constant band of data occurring between 11 am and 12:30 pm. The constant band period in Day 6, being depicted as having a constant, non varying signal input from a CGM of 50 mg/dl of sensed glucose over an hour and half, quickly and efficiently indicates to a user (having no episode of hypoglycemia) that the sensor of the CGM was either malfunctioning or not seated properly during that period, but that overall the diabetes control therapy of the user was good as represented by the remaining plotted data for the Day 6 trace. Although in FIG. 16B, a sensor malfunction or improper sensor seating is shown as a constant sensed glucose value, such issues may also be shown as a deadband period of no signal input, with a period having a value of zero (or some other spurious constant value) depicted in the plotted data. However, if the user did have an episode of hypoglycemia during the constant period between 11 am and 12:30 pm, the found distinct cluster indicates to the user as well as to an observing healthcare professional (HCP) that the diabetes control therapy is not effective in the period after the morning meal and before the lunch meal, as the user's glucose dipped below an alarm level (i.e., 50 mg/dl) of the CGM, thereby causing the constant band period in Day 6.

Figure 16C:
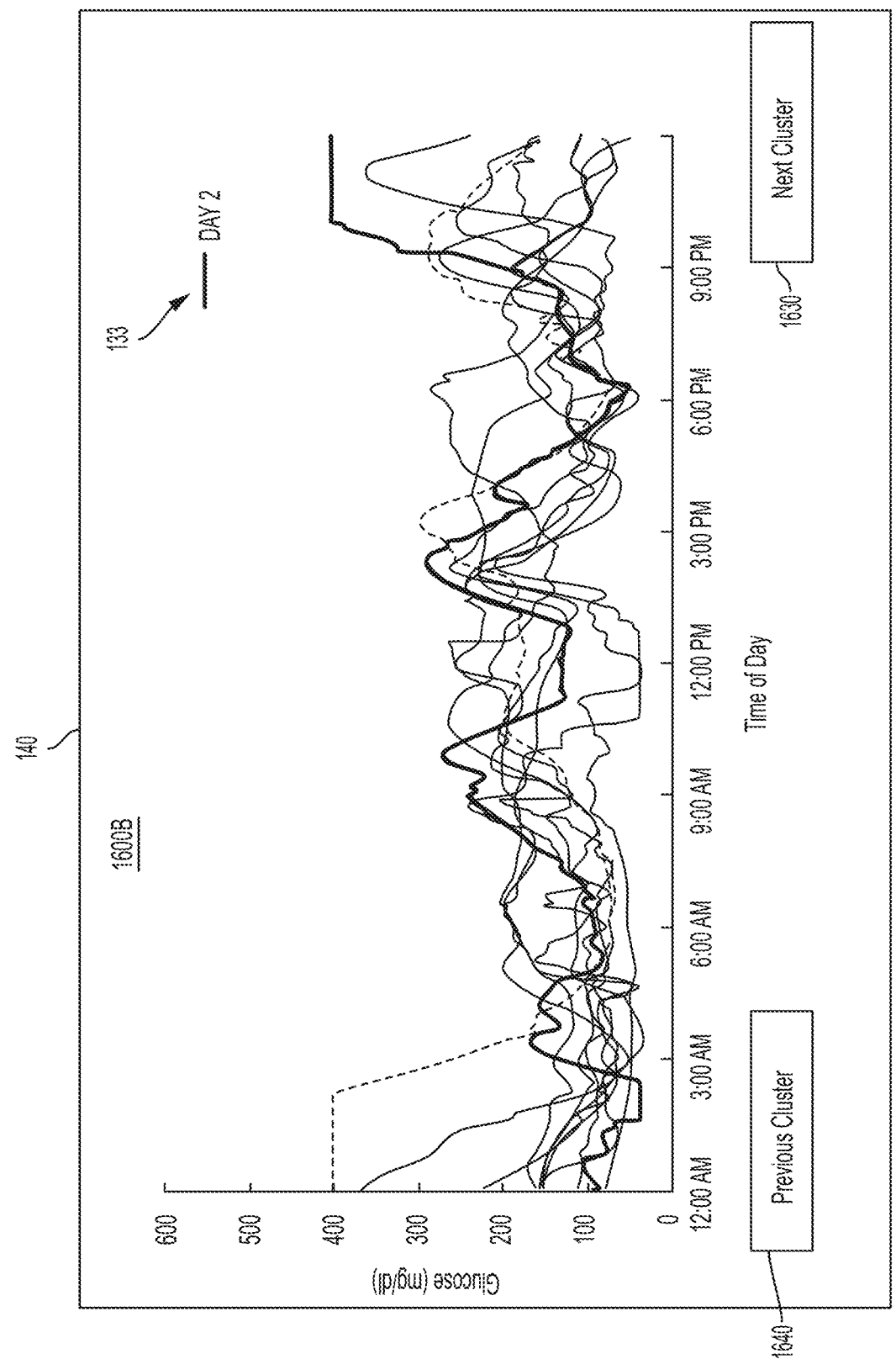
Figure 16D:
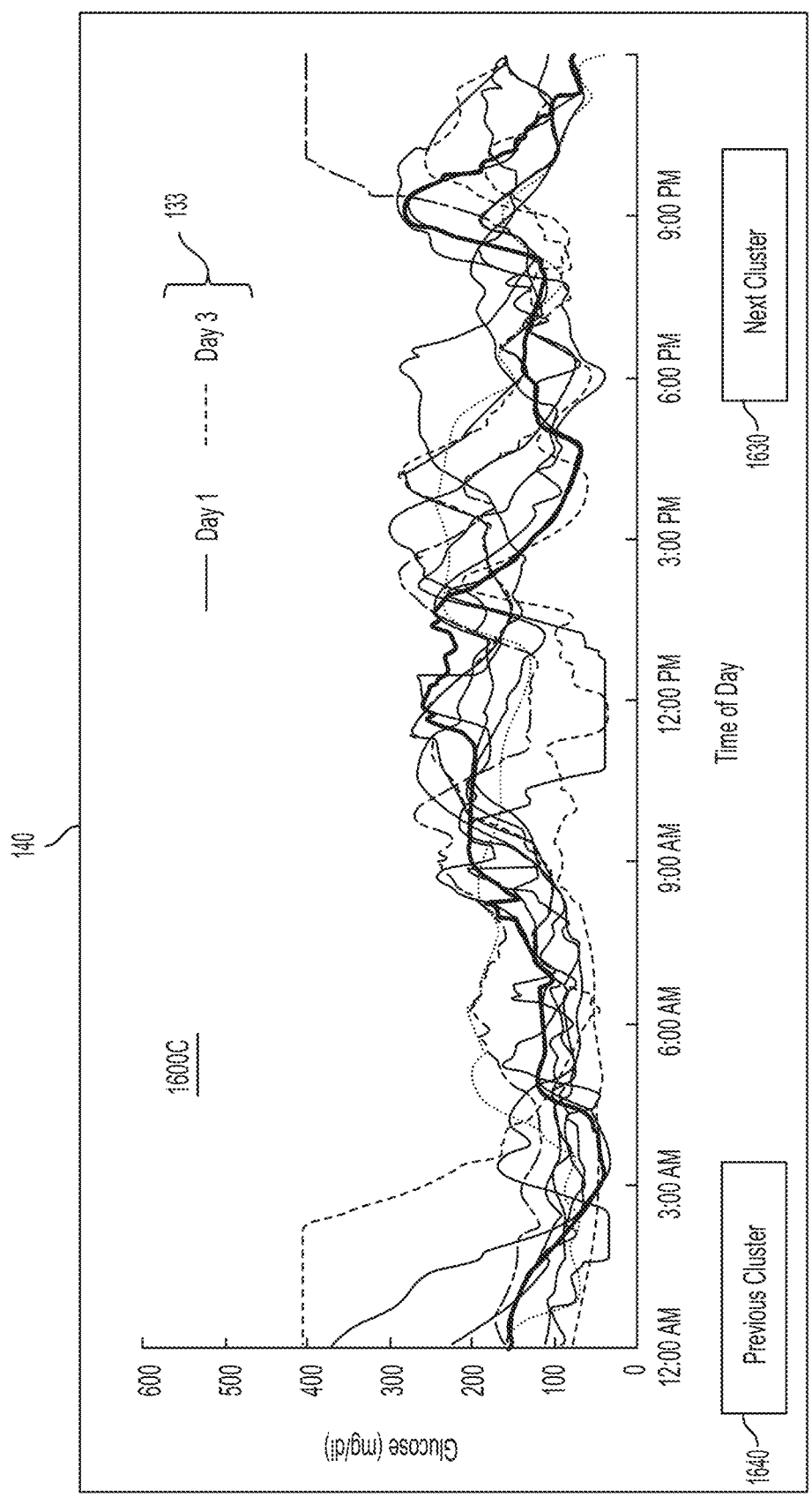
Figure 16E:
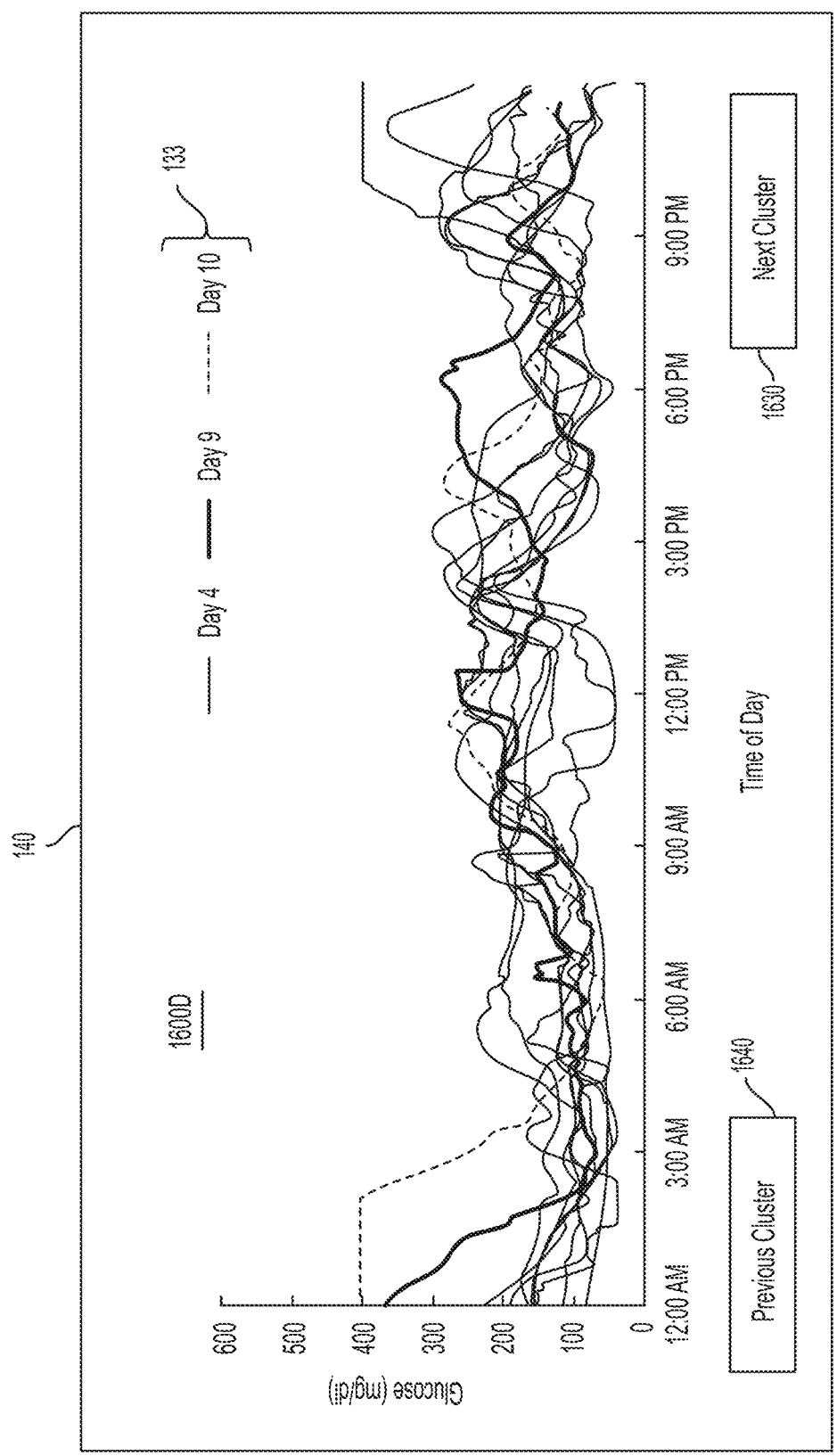
Figure 16F:
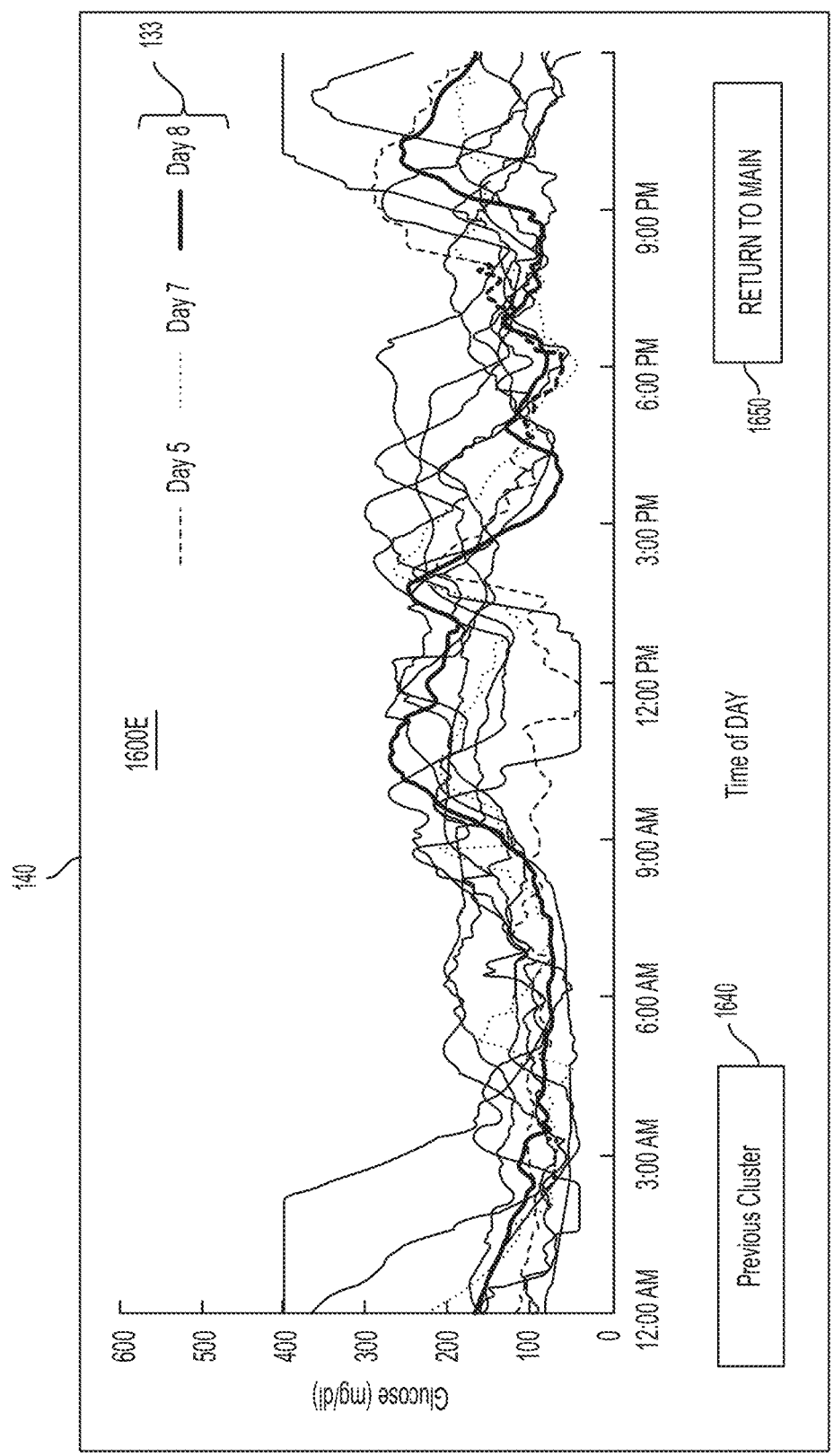

Likewise, as indicated in the next distinct cluster 1600B depicted by FIG. 16C, in the case of no sensor malfunctioning/seating problem, it is quickly discernible from this cluster that the user suffered both a period of hypoglycemia, which occurred during the sleeping period fast between 1:30 am and 2:30 am, and a period of hyperglycemia, which occurred after 9 pm as the user's glucose raised over an alarm level (i.e., 400 mg/dl) of the CGM, thereby causing the constant band period at 400 mg/gl in Day 2. Although the sufficiency of the diabetes control therapy of the user over the rest of the Day 2 trace is generally good, attention/changes in the therapy control routine and/or lifestyle of the diabetic user may be needed at least in these two periods. Such is also indicated in the next distinct cluster comprised of the Day 1 and Day 3 traces, which have periods of or near hyperglycemia before or immediately after midnight. Although, such episodes may be easily explained, such as if those days represented periods in which the diabetic user ignored diet constraints, repeats in such episodes clearly indicated an issue that should be address in the diabetes control therapy of the user. Recommendations of how the above issues in the diabetes control therapy should be address is also made evident by the clustering. For example, the user should model/mimic/follow the diabetes control therapy used on Days 4, 9 and 10 as the next distinct cluster 1600D depicted by FIG. 16E as well as for the next (and last) distinct 1600E depicted by FIG. 16F for Days 5, 7, and 8, clearly shows that on these six days the user's diabetes control therapy was adequate, with no issues/periods of hypo- or hyperglycemia.

To conveniently and quickly view the found distinct clusters 1600A, 1600B, 1600C, 1600D and 1600E, e.g. from an initial data (dump) plot 1605 display of the dataset 131 depicted by FIG. 16A, one or more buttons (e.g., Close and View Clusters) 1610 and 1620 of a user interface 1625 is displayed with the plotted data. A user selecting the "Close" button 1610, either with a finger, stylus or a cursor, will cause the processor 120 to close the displayed plot 1605 and return to a previous/default display image of the device 105. A user selecting the "View Cluster" button 1620, either with a finger, stylus or a cursor, will cause the processor 120 to display the first found distinct cluster, e.g., cluster 1600A depicted by FIG. 16B. The user interface 1625 has a number of buttons, such as a "Next Cluster" button 1630 to cause the processor 120 to display the next found distinct cluster, such as cluster 1600B, a "Previous Cluster" button 1640 (FIG. 16C) to cause the processor 120 to display the previously displayed distinct cluster, and a "Return to Main" button 1650 (FIG. 16E) to cause the processor 120 to return to display the initial data plot 1605 (FIG. 16A). In other embodiments, the user interface 1625 may display along with each cluster, buttons 1610, 1630, 1640 and 1650 for ease of navigation.

In view of the above disclosure, it is apparent that in one embodiment disclosed is a patient diabetes monitoring system for a patient. The system comprises a physiological data input device which acquires a plurality of physiological measurements of the patient within a time window to generate at least one time window dataset of collected unsupervised daily monitoring profiles; a memory storing an unsupervised daily monitoring profile clustering algorithm; and a processor in communication with said input device to receive said generated at least one time window dataset, and in communication with said memory in order to execute said unsupervised daily monitoring profile clustering algorithm, wherein said unsupervised daily monitoring profile clustering algorithm when executed by said processor causes said processor automatically to: pre-process the dataset to control an amount of bias/aggressiveness from the collected unsupervised daily monitoring profiles to generate a pre-processed dataset, build a similarity matrix from the pre-processed dataset, and output an optimum number of similarity clusters found by the processor from the similarity matrix. In another embodiment of the system, the pre-processing of the dataset controls the amount of bias/aggressiveness via a data transformation of the dataset that makes the pre-processed dataset symmetric for retrospective analysis. In another embodiment of the system the data transformation for retrospective analysis result from processing by the dataset with a hazard function defined by: $G_t = \alpha * \ln(G-\beta) - \alpha * \ln(\alpha)$, where parameter $\alpha = T_c - \beta$, and parameter $\beta = D_r - 1$, in which is a center of a transformed space, $D_r$ is a minimum defined glucose level, $G_t$ is the transformed data of blood glucose concentration measurements provided in the dataset, and "g" is original glucose level values of the blood glucose concentration measurements provided in the dataset and measured in millimoles per liter. In another embodiment of the system, the physiological data input device is a CGM.

In another embodiment of the above mentioned system, after the pre-processing of the dataset, the pre-processed dataset is then processed to build the similarity matrix to account for time-series dynamics in the pre-processed dataset. In another embodiment of the system, the time-series dynamics in the pre-processed dataset is accounted for by a distance matrix that accounts for glucose value levels in an actual space or transformed space as well as via a rate of change of the glucose value levels to compute a distance between each pair of similar time series of data presented in the pre-processed dataset. In another embodiment of the system, the distance matrix is defined by: $d(X_i, Y_i) = k*|X_i - Y_i| + (1-k)*|(m_x - m_y)*(X_i - Y_i)|$, where, $X_i$ is a glucose level value in a first time series X at time i, $Y_i$ is a glucose value in a second time series Y at time i, k is a weighing factor, $m_x$ is the slope at time i for the first time series $X_i$, and $m_y$ is the slope at time i for time series $X_i$. In another embodiment of the system, a sum of distances between the first and second time series X and Y is used in an elastic alignment procedure to account for varying temporal responses/shifts in the pre-processed dataset. In another embodiment of the system, the elastic alignment procedure is a dynamic time warping process which allows for elastic matching of the first and second time series X and Y by local compression or elongation along a time axis. In another embodiment of the system, the dynamic time warping process results in any penalty being added to the sum of the distances between the first and second time series X and Y. In another embodiment of the system, the first and second time series are CGM curves. In another embodiment of the system, the first and second time series X and Y of the pre-processed dataset are processed by the processor with the penalty as follows:

(a) Start at origin, distance between curves of the first time series X and the second time series Y is: $X(1,1) = Y(1,1)$;

(b) Keep first row a constant distance by: $X(i,1) = X(i-1, 1) + Y(i,1)$;

(c) Keep first column constant by: $X(1,j) = X(1,j-1) + Y(1, j)$; and (d) Carry on for next row and next column to end of search space of the pre-processed dataset as defined by: $X(i,j) = \min(X(i,j-1), X(i-1,j-1), X(i-1,j)) + Y(i,j)$.

In another embodiment of the above disclosed system, output of the build a similarity matrix process is checked against one or more conditions to evaluate if a determined alignment path is a valid path, the one or more conditions being: monotonicity, continuity, boundary conditions, search window, and slope. In another embodiment of the system, output of the similarity matrix process is then used in an agglomerative clustering process to output similarity clusters, the agglomerative clustering process having the following pseudo code:

(a) Compute a distance matrix between data points of the output;
(b) Let each of the data points be a cluster;
(c) Repeat following:
   i. Merge two closest clusters, and
   ii. Update the distance matrix; and
(d) Do Repeat until only a single cluster remains.

In another embodiment of the system, an inflection point in the distance matrix is calculated by the processor to find the optimal minimum number of clusters. In another embodiment of the system, if d(l) is a distance curve in the distance matrix, d'(l) is a first derivative of the distance curve, and d"(l) is a second derivative of the distance curve, and if d'(l) exists, then the optimal minimum number of clusters along the curve d(l) is calculated by the processor to be a point l where d"(l)=0. In another embodiment of the system, the processor calculates the inflection point as follows:
(a) Let first k points on the distance curve d(l) with p points be 1, 2, ... k, and find slopes:
   $m_1 = d(2)-d(1)/(2-1)$, $m_2 = d(3)-d(1)/(3-1)$, ..., $m_k = d(n)-d(1)/(n-1)$;
(b) Calculate median of slopes from step (a): $m_a$=median $(m_1, m_2 ... m_k)$;
(c) Let last n points on the distance curve d(l) with p points be p-n, ..., p-1, p, and find slopes:
   $m_p = d(p)-d(p-1)/(p-(p-1))$, $m_2 = d(p)-d(p-2)/(p-(p-2))$, ..., $m_n = d(p)-d(p-n)/(p-(p-n))$; and
(d) Calculate median of slopes from step (c): $m_b$=median $(m_1, m_2 ... m_n)$,
where a first line defined by the median slope $m_a$ with a starting point as the first point along the distance curve d(l), and second line being defined by the median slope $m_b$ with a starting point as the end point along the distance curve d(l), the inflection point being a projection of an intersection point between the first and second lines on the distance curve d(l) denoted by $l_p$, and if inflection point $l_p$ is not an integer, then the optimal minimum number of clusters $L_{min}$ is found by:

$$L_{min} = \begin{cases} \text{floor}(lp) & \text{if } abs(l_p - \text{floor}(l_p)) < abs(l_p - \text{ceil}(l_p)) \\ \text{ceil}(lp) & \text{if } abs(l_p - \text{floor}(l_p)) > abs(l_p - \text{ceil}(l_p)) \end{cases}.$$

In still another embodiment, disclosed is a non-transitory computer-readable medium that stores a program that, when executed by a processor, causes the processor to execute, via a patient diabetes monitoring system having a physiological data input device which acquires a plurality of physiological measurements of the patient within a time window to generate at least one time window dataset of collected unsupervised daily monitoring profiles and which is in communication with said processor, such that said processor receives said generated at least one time window dataset, and in communication with said memory, an unsupervised daily monitoring profile clustering algorithm that causes said processor to automatically: pre-process the dataset to control an amount of bias/aggressiveness from the collected unsupervised daily monitoring profiles to generate a pre-processed dataset, build a similarity matrix from the pre-processed dataset, and output an optimum number of similarity clusters. In another embodiment of the non-transitory computer-readable medium, CGM profile or insulin profile is the at least one time window dataset from a patient, and comprises raw data, transformed data, raw data associated with related data tags, transformed data associated with related data tags, or combinations thereof.

In yet another embodiment, disclosed is a method for identifying day(s) where a diabetes control therapy was inadequate for a patient using a monitoring system comprising a display device, a physiological data input device and a processor. The method comprises receiving automatically from physiological data input device a plurality of physiological measurements of the patient within a time window to generate at least one time window dataset of collected unsupervised daily monitoring profiles; and executing from a memory a stored an unsupervised daily monitoring profile clustering algorithm and causing the processor automatically to: pre-process the dataset to control an amount of bias/aggressiveness from the collected unsupervised daily monitoring profiles, thereby generating a pre-processed dataset, build a similarity matrix from the pre-processed dataset, and output on the display an optimum number of similarity clusters found by the processor from the similarity matrix.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and understood not to be limited to the details of structure and operation shown and described in the specification and drawings.

What is claimed is:

1. A patient diabetes monitoring system for a patient comprising:
   a physiological data input device which acquires a plurality of blood glucose concentration measurements of the patient within a time window to generate at least one time window dataset of collected unsupervised daily monitoring profiles;
   a memory storing an unsupervised daily monitoring profile clustering algorithm; and
   a processor in communication with said input device to receive said generated at least one time window dataset, and in communication with said memory in order to execute said unsupervised daily monitoring profile clustering algorithm,
   wherein said unsupervised daily monitoring profile clustering algorithm when executed by said processor causes said processor automatically to:

pre-process the dataset to generate a pre-processed dataset via a data transformation of the dataset that makes the pre-processed dataset symmetric for retrospective analysis, build a similarity matrix from the pre-processed dataset, and output an optimum number of similarity clusters found by the processor from the similarity matrix, wherein the data transformation for retrospective analysis results from processing the dataset with a hazard function defined by: $G_t=\alpha*\ln(G-\beta)-\alpha*\ln(\alpha)$, where parameter $\alpha=T_c-\beta$, and parameter $\beta=D_r-1$, in which $T_c$ is a center of a transformed space, $D_r$ is a minimum defined glucose level, $G_t$ is the transformed data of the blood glucose concentration measurements provided in the dataset, and G is original glucose level values of the blood glucose concentration measurements provided in the dataset and measured in millimoles per liter.

2. The system of claim 1, wherein after the pre-processing of the dataset, the pre-processed dataset is then processed to build the similarity matrix to account for time-series dynamics in the pre-processed dataset.

3. The system of claim 2, wherein the time-series dynamics in the pre-processed dataset is accounted for by a distance matrix that accounts for glucose value levels in an actual space or transformed space as well as via a rate of change of the glucose value levels to compute a distance between each pair of similar time series of data presented in the pre-processed dataset.

4. The system of claim 3, wherein the distance matrix is defined by:

$$d(X_i,Y_i)=k*|X_i-Y_i|+(1-k)*|(m_x-m_y)*(X_i-Y_i)|,$$

where, $X_i$ is a glucose level value in a first time series X at time i, $Y_i$ is a glucose value in a second time series Y at time i, k is a weighing factor, $m_x$ is the slope at time i for the first time series $X_i$, and $m_y$ is the slope at time i for time series $X_i$.

5. The system of claim 4, wherein a sum of distances between the first and second time series X and Y is used in an elastic alignment procedure to account for varying temporal responses/shifts in the pre-processed dataset.

6. The system of claim 5, wherein the elastic alignment procedure is a dynamic time warping process which allows for elastic matching of the first and second time series X and Y by local compression or elongation along a time axis.

7. The system of claim 6, wherein the dynamic time warping process results in any penalty being added to the sum of the distances between the first and second time series X and Y.

8. The system of claim 7, wherein the first and second time series are continuous glucose monitor (CGM) curves.

9. The system of claim 7, wherein the first and second time series X and Y of the pre-processed dataset are processed by the processor with the penalty as follows:

(a) Start at origin, distance between curves of the first time series X and the second time series Y is: $X(1,1)=Y(1,1)$;

(b) Keep first row a constant distance by: $X(i,1)=X(i-1,1)+Y(i,1)$;

(c) Keep first column constant by: $X(1,j)=X(1,j-1)+Y(1,j)$; and (d) Carry on for next row and next column to end of search space of the pre-processed dataset as defined by: $X(i, j)=\min(X(i, j-1), X(i-1, j-1), X(i-1, j))+Y(i, j)$.

10. The system of claim 1, wherein output of the build a similarity matrix process is checked against one or more conditions to evaluate if a determined alignment path is a valid path, the one or more conditions being: monotonicity, continuity, boundary conditions, search window, and slope.

11. The system of claim 10, wherein output of the similarity matrix process is then used in an agglomerative clustering process to output similarity clusters, the agglomerative clustering process having the following pseudo code:

(a) Compute a distance matrix between data points of the output;

(b) Let each of the data points be a cluster;

(c) Repeat following:
  i. Merge two closest clusters, and
  ii. Update the distance matrix; and (d) Do Repeat until only a single cluster remains.

12. The system of claim 11, wherein an inflection point in the distance matrix is calculated by the processor to find the optimal minimum number of clusters.

13. The system of claim 12, wherein if d(l) is a distance curve in the distance matrix, d'(l) is a first derivative of the distance curve, and d''(l) is a second derivative of the distance curve, and if d'(l) exists, then the optimal minimum number of clusters along the curve d(l) is calculated by the processor to be a point l where d''(l)=0.

14. The system of claim 12, wherein the processor calculates the inflection point as follows:

(a) Let first k points on the distance curve d(l) with p points be 1, 2, . . . k, and find slopes:

$$m_1=d(2)-d(1)/(2-1), m_2=d(3)-d(1)/(3-1), \ldots, m_k=d(n)-d(1)/(n-1);$$

(b) Calculate median of slopes from step ($\alpha$): $m_a$=median $(m_1, m_2 \ldots m_k)$;

(c) Let last n points on the distance curve d(l) with p points be p-n, . . . , p-1, p, and find slopes: $m_p=d(p)-d(p-1)/(p-(p-1))$, $m_2=d(p)-d(p-2)/(p-(p-2))$, . . . , $m_n=d(p)-d(p-n)/(p-(p-n))$; and (d) Calculate median of slopes from step (c): $m_b$=median $(m_1, m_2 \ldots m_n)$, where a first line defined by the median slope $m_a$ with a starting point as the first point along the distance curve d(l), and second line being defined by the median slope $m_b$ with a starting point as the end point along the distance curve d(l), the inflection point being a projection of an intersection point between the first and second lines on the distance curve d(l) denoted by $l_p$, and if inflection point $l_p$ is not an integer, then the optimal minimum number of clusters $L_{min}$ is found by:

$$L_{min} = \begin{cases} \text{floor}(lp) & \text{if } \text{abs}(l_p - \text{floor}(l_p)) < \text{abs}(l_p - \text{ceil}(l_p)) \\ \text{ceil}(lp) & \text{if } \text{abs}(l_p - \text{floor}(l_p)) > \text{abs}(l_p - \text{ceil}(l_p)) \end{cases}.$$

15. The system of claim 1, wherein the physiological data input device is a continuous glucose monitor (CGM).

16. A non-transitory computer-readable medium that stores a program that, when executed by a processor, causes the processor to execute, via a patient diabetes monitoring system having a physiological data input device which acquires a plurality of blood glucose concentration measurements of the patient within a time window to generate at least one time window dataset of collected unsupervised daily monitoring profiles and which is in communication with said processor, such that said processor receives said generated at least one time window dataset, and in communication with said memory, an unsupervised daily monitoring profile clustering algorithm that causes said processor to automatically:

pre-process the dataset to generate a pre-processed dataset via a data transformation of the dataset that makes the pre-processed dataset symmetric for retrospective analysis, build a similarity matrix from the pre-processed dataset, and output an optimum number of similarity clusters, wherein the data transformation for retrospective analysis results from processing the dataset with a hazard function defined by: $G_t=\alpha*\ln(G-\beta)-\alpha*\ln(\alpha)$, where parameter $\alpha=T_c-\beta$, and parameter $\beta=D_r-1$, in which $T_c$ is a center of a transformed space, $D_r$ is a minimum defined glucose level, $G_t$ is the transformed data of the blood glucose concentration measurements provided in the dataset, and G is original glucose level values of the blood glucose concentration measurements provided in the dataset and measured in millimoles per liter.

17. The non-transitory computer-readable medium of claim 16, wherein the at least one time window dataset from a patient is a continuous glucose monitor (CGM) profile, and wherein said continuous glucose monitor (CGM) profile comprises raw data, transformed data, raw data associated with related data tags, transformed data associated with related data tags, or combinations thereof.

18. A method for identifying day(s) where a diabetes control therapy was inadequate for a patient using a monitoring system comprising a display device, a physiological data input device and a processor, the method comprising:

receiving automatically from the physiological data input device a plurality of blood glucose concentration measurements of the patient within a time window to generate at least one time window dataset of collected unsupervised daily monitoring profiles; and executing from a memory a stored an unsupervised daily monitoring profile clustering algorithm and causing the processor automatically to:

pre-process the dataset to generate a pre-processed dataset via a data transformation of the dataset that makes the pre-processed dataset symmetric for retrospective analysis, build a similarity matrix from the pre-processed dataset, and output on the display an optimum number of similarity clusters found by the processor from the similarity matrix, wherein the data transformation for retrospective analysis results from processing the dataset with a hazard function defined by: $G_t=\alpha*\ln(G-\beta)-\alpha*\ln(\alpha)$, where parameter $\alpha=T_c-\beta$, and parameter $\beta=D_r-1$, in which $T_c$ is a center of a transformed space, $D_r$ is a minimum defined glucose level, $G_t$ is the transformed data of the blood glucose concentration measurements provided in the dataset, and G is original glucose level values of the blood glucose concentration measurements provided in the dataset and measured in millimoles per liter.

* * * * *